US006846791B1

(12) United States Patent
Dupont et al.

(10) Patent No.: US 6,846,791 B1
(45) Date of Patent: Jan. 25, 2005

(54) LAUNDRY DETERGENT COMPOSITIONS COMPRISING HYDROPHOBICALLY MODIFIED POLYAMINES

(75) Inventors: Jeffrey Scott Dupont, Cincinnati, OH (US); Eugene Paul Gosselink, Cincinnati, OH (US); Kenneth Nathan Price, Wyoming, OH (US); Robert Henry Rohrbaugh, Indian Springs, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 66 days.

(21) Appl. No.: 10/129,617

(22) PCT Filed: Nov. 7, 2000

(86) PCT No.: PCT/US00/30644

§ 371 (c)(1),
(2), (4) Date: May 8, 2002

(87) PCT Pub. No.: WO01/34739

PCT Pub. Date: May 17, 2001

Related U.S. Application Data

(60) Provisional application No. 60/164,491, filed on Nov. 9, 1999.

(51) Int. Cl.$^7$ .............................. C11D 1/22; C11D 1/83; C11D 3/26; C11D 3/395; C11D 3/30

(52) U.S. Cl. ..................... 510/303; 510/309; 510/310; 510/311; 510/312; 510/336; 510/340; 510/341; 510/350; 510/351; 510/356; 510/360; 510/372; 510/376; 510/378; 510/499

(58) Field of Search .................... 510/303, 309, 510/310, 311, 312, 336, 340, 341, 350, 351, 356, 360, 499, 372, 376, 378; 8/111, 137

(56) References Cited

U.S. PATENT DOCUMENTS

| 3,234,258 | A | 2/1966 | Morris |
| 3,929,678 | A | 12/1975 | Laughlin et al. |
| 4,412,934 | A | 11/1983 | Chung et al. |
| 4,430,243 | A | 2/1984 | Bragg |
| 4,565,647 | A | 1/1986 | Llenado |
| 4,634,551 | A | 1/1987 | Burns et al. |
| 4,659,802 | A | 4/1987 | Rubingh et al. |
| 4,728,455 | A | 3/1988 | Rerek |
| 4,810,410 | A | 3/1989 | Daikun et al. |
| 4,966,723 | A | 10/1990 | Hodge et al. |
| 5,075,041 | A | 12/1991 | Lutz |
| 5,114,606 | A | 5/1992 | VanVliet et al. |
| 5,114,611 | A | 5/1992 | VanKralingen et al. |
| 5,130,045 | A | 7/1992 | Mitchell et al. |
| 5,153,161 | A | 10/1992 | Kerschner et al. |
| 5,194,416 | A | 3/1993 | Jureller et al. |
| 5,227,084 | A | 7/1993 | Maretens et al. |
| 5,244,594 | A | 9/1993 | Favre et al. |
| 5,246,612 | A | 9/1993 | VanDijk et al. |
| 5,246,621 | A | 9/1993 | Favre et al. |
| 5,256,779 | A | 10/1993 | Kerschner et al. |
| 5,274,147 | A | 12/1993 | Kerschner et al. |
| 5,280,117 | A | 1/1994 | Kerschner et al. |
| 5,284,944 | A | 2/1994 | Madison et al. |
| 5,349,101 | A | 9/1994 | Lutz et al. |
| 5,389,277 | A | 2/1995 | Prieto |
| 5,405,412 | A | 4/1995 | Willey et al. |
| 5,405,413 | A | 4/1995 | Willey et al. |
| 5,460,747 | A | 10/1995 | Gosselink et al. |
| 5,503,639 | A | 4/1996 | Willey et al. |
| 5,523,434 | A | 6/1996 | Burns et al. |
| 5,576,282 | A | 11/1996 | Miracle et al. |
| 5,578,136 | A | 11/1996 | Taylor et al. |
| 5,584,888 | A | 12/1996 | Miracle et al. |
| 5,595,967 | A | 1/1997 | Miracle et al. |
| 5,597,936 | A | 1/1997 | Perkins et al. |
| 5,654,421 | A | 8/1997 | Taylor et al. |
| 5,686,014 | A | 11/1997 | Baillely et al. |
| 5,686,015 | A | 11/1997 | Willey et al. |
| 5,686,401 | A | 11/1997 | Willey et al. |
| 5,695,679 | A | 12/1997 | Christie et al. |
| 5,698,504 | A | 12/1997 | Christie et al. |
| 5,703,030 | A | 12/1997 | Perkins et al. |
| 5,998,350 | A | 12/1999 | Burns et al. |
| 6,071,871 | A | 6/2000 | Gosselink et al. |
| 6,121,226 | A | 9/2000 | Gosselink |
| 6,291,415 | B1 | 9/2001 | Watson et al. |
| 6,444,633 | B2 * | 9/2002 | Price .......................... 510/299 |
| 6,472,359 | B1 * | 10/2002 | Ghosh ........................ 510/321 |
| 6,479,451 | B2 * | 11/2002 | Price .......................... 510/321 |
| 6,525,012 | B2 * | 2/2003 | Price et al. ................. 510/321 |

FOREIGN PATENT DOCUMENTS

| EP | 0 544 440 A2 | 6/1993 |
| EP | 0 544 490 A1 | 6/1993 |
| EP | 0 549 271 A1 | 6/1993 |
| EP | 0 549 272 A1 | 6/1993 |
| WO | WO 94/28102 | 12/1994 |
| WO | WO 98/39406 A1 | 9/1998 |
| WO | WO 99/06519 | 2/1999 |

OTHER PUBLICATIONS

*Bleaching Agents*, Kirk Othmer's Encyclopedia of Chemical Technology, 4$^{th}$ ed., 1992, pp. 271–300.

Surfactant Science Series 1, Chapter 8, 1967, pp. 208–246.

Surfactant Science Series 19, Chapter 1, 1987, pp. 3–28.

Wieranga et al., *Synthesis and Characterization of Cobalt (III) Nicotinic Acid Complexes*, Inorganic Chemistry, vol. 21, 1982, pp. 2881–2885.

(List continued on next page.)

*Primary Examiner*—Gregory R. Del Cotto
(74) *Attorney, Agent, or Firm*—Laura R. Grunzinger; James F. McBride; Kim William Zerby

(57) ABSTRACT

The present invention relates to hydrophobically modified polyamines and laundry detergent compositions comprising such polyamines and a surfactant system. In addition to traditional cleaning benefits, such compositions provide enhanced greasy soil removal capabilities.

12 Claims, No Drawings

OTHER PUBLICATIONS

Jackman et al., *Synthesis of Transition–Metal Carboxylato Complexes*, Inorganic Chemistry, vol. 18, No. 6, 1979, pp. 1497–1502.

*Notes*, Inorganic Chemistry, vol. 18, No. 7, 1979, pp. 2023–2025.

Basolo et al., *Mechanism of Substitution Reactions in Complex Ions*, Journal of Physical Chemistry, vol. 56, 1952, pp. 22–25.

Inorganic Synthesis, vol. VI, 1960, pp. 173–176.

Williams et al., *Coordination Complexes of Cobalt*, Journal of Chemical Education, vol. 66, No. 12, 1989, pp. 1043–1045.

Tobe, *Base Hydrolysis of Transition–Metal Complexes*, Adv. Inorg. Bioinorg. Mech., vol. 2, 1983, pp. 1–94.

Jolly, The Synthesis and Characterization of Inorganic Compounds, 1970, pp. 461–463.

W.L. Jolly, *The Synthesis and Characterization of Inorganic Compounds*, Prentice–Hall, 1970, pp. 461–463.

U.S. Appl. No.10/129,618, filed May 8, 2002, Gosselink et al.

U.S. Appl. No.09/789,774, filed Feb. 21, 2001, Price et al.

U.S. Appl. No.09/790,044, filed Feb. 21, 2001, Ghosh.

U.S. Appl. No.09/790,042, filed Feb. 21, 2001, Price.

U.S. Appl. No.09/789,443, filed Feb. 21, 2001, Price.

\* cited by examiner

LAUNDRY DETERGENT COMPOSITIONS COMPRISING HYDROPHOBICALLY MODIFIED POLYAMINES

CROSS REFERENCE TO RELATED APPLICATIONS

This application claims the benefit of PCT International Application Ser. No. PCT/US00/30644, filed Nov. 7, 2000, which claims the benefit of U.S. Provisional Application Ser. No. 60/164,491 filed on Nov. 9, 1999, (now abandoned).

FIELD OF THE INVENTION

The present invention relates to laundry detergent compositions comprising one or more hydrophobically modified polyamines which provide enhanced lipid soil removal benefits, inter alia, body soil removal. The present invention further relates to nil surfactant laundry detergent compositions wherein aqueous solutions of hydrophobically modified polyamines are the foundation for laundry detergent compositions. The present invention also relates to methods for removing body soil from fabric, inter alia, the collars of wearing apparel.

BACKGROUND OF THE INVENTION

Fabric, especially clothing, can become soiled with a variety of foreign substances ranging from hydrophobic stains (grease, oil) to hydrophilic stains (clay). The level of cleaning necessary to remove foreign substances depends to a large degree upon the amount of stain which is present and to the degree and manner in which the foreign substance has contacted the fabric fibers. Grass stains usually involve direct abrasive contact with vegetative matter thereby producing highly penetrating stains. Human body oils and perspiration are continually produced and deposited onto fabric while clothing is being worn, especially at the collar, cuffs, and underarm areas. Body oils become embedded into the fabric not only by absorption or by wicking of the materials themselves into the fiber, but also by the mechanical action of the body against the fabric.

In many cases a surfactant per se is not all that is necessary to remove unwanted hydrophobic soils and stains. In the case of human body oils and other hydrophobic stains on collars, cuffs and other contact areas, perspiration and body oil stains are not fully removed by washing alone. Even hand scrubbing of collars does not ameliorate the dingy appearance of white cotton-comprising fabric. For hydrophobic soils, dispersants are ineffective because they act on soils which are removed and not on those which are embedded throughout the fabric surface fibers. Formulators have used soil release polymers to attenuate the spreading ut and absorption f greasy, ily material onto synthetic fabric, however, cellulosic fiber still presents the laundry formulator with the problem of dingy appearance due to human body oils and perspiration stains.

There is a long felt need in the art for laundry detergent compositions which can effectively solublize greasy, oily materials from the surface fibers of fabric, and once solublized, said oily materials can then be eliminated by the action of surfactants. There is also a long felt need for a cleaning system which effectively removes lipid type stains which have been worn into fabric by mechanical action of skin against fabric, for example, at shirt collars and cuffs.

SUMMARY OF THE INVENTION

It has now been surprisingly discovered that laundry detergent compositions comprising certain quaternized polyamines have enhanced greasy soil removal benefits. The polyamines of the present invention are fully quaternized alkyleneoxylated, preferably ethyleneoxylated, polyamines having hydrophobic backbone spacers between the backbone nitrogen atoms. Surprisingly the choice of a hydrophobic quaternizing agent provides enhanced removal of greasy, oily stains on clothing either in the presence of detersive surfactants or in the absence of surfactants. The laundry detergent compositions of the present invention are especially effective in removing "ground-in oily stains", inter alia, perspiration underarm stains, body oils at the collar and cuffs of shirts. When used together with a suitable surfactant system, the hydrophobically modified polyamines of the present invention provides for removal of stains which were once believed ruinous to fabric, especially cellulose comprising fabric.

The first aspect of the present invention relates to a hydrophobically modified polyamine having the formula:

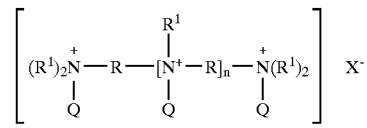

wherein R is $C_6$–$C_{12}$ linear or branched alkylene, and mixtures thereof; $R^1$ is an alkyleneoxy unit having the formula:

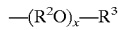

wherein $R^2$ is $C_2$–$C_4$ linear or branched alkylene, and mixtures thereof; $R^3$ is hydrogen, benzyl, and mixtures thereof; x is from about 15 to about 30; Q is a hydrophobic quaternizing unit selected from the group consisting of $C_8$–$C_{30}$ linear or branched alkyl, $C_6$–$C_{30}$ cycloalkyl, $C_7$–$C_{30}$ substituted or unsubstituted alkylenearyl, and mixtures thereof; X is an anion present in sufficient amount to provide electronic neutrality; n is from 0 to 3.

The present invention further relates to laundry detergent compositions comprising:

A) from about 0.01%, preferably from about 0.1%, more preferably from about 1%, most preferably from about 3% to about 50%, preferably to about 20%, more preferably to about 10%, most preferably to about 7% by weight, of a hydrophobically modified polyamine having the formula:

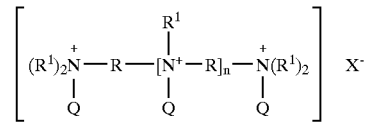

wherein R is $C_6$–$C_{20}$ linear or branched alkylene, and mixtures thereof; $R^1$ is an alkyleneoxy unit having the formula:

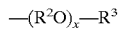

wherein $R^2$ is $C_2$–$C_4$ linear or branched alkylene, and mixtures thereof; $R^3$ is hydrogen, $C_1$–$C_{22}$ alkyl, $C_7$–$C_{22}$ alkylenearyl, and mixtures thereof; x is from about 15 to about 30; Q is a hydrophobic quaternizing unit selected from the group consisting of $C_8$–$C_{30}$ linear or branched alkyl, $C_6$–$C_{30}$ cycloalkyl, $C_7$–$C_{30}$ substituted or unsubstituted alkylenearyl, and mixtures thereof; X is an anion present in sufficient amount to provide electronic neutrality; n is from 0 to 3;

B) from about 0.01% by weight, of a surfactant system comprising one or more surfactants selected from:
  i) from 0% to 100% by weight, of one or more anionic surfactants;
  ii) from 0% to 100% by weight, of one or more nonionic surfactants;
  iii) optionally from 0.1% to about 80% by weight, of one or more cationic surfactants;
  iv) optionally from 0.1% to about 80% by weight, of one or more zwitterionic surfactants;
  v) optionally from 0.1% to about 80% by weight, of one or more ampholytic surfactants; or
  vi) mixtures thereof;

C) the balance carriers and adjunct ingredients.

The present invention further relates to a nil surfactant laundry or cleaning composition comprising:

a) from about 0.01%, preferably from about 0.1%, more preferably from about 1%, most preferably from about 3% to about 50%, preferably to about 20%, more preferably to about 10%, most preferably to about 7% by weight, of a hydrophobically modified polyamine having the formula:

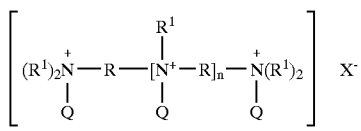

wherein R is $C_6$–$C_{20}$ linear or branched alkylene, and mixtures thereof; $R^1$ is an alkyleneoxy unit having the formula:

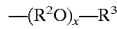

wherein $R^2$ is $C_2$–$C_4$ linear or branched alkylene, and mixtures thereof; $R^3$ is hydrogen, $C_1$–$C_{22}$ alkyl, $C_7$–$C_{22}$ alkylenearyl, and mixtures thereof; x is from about 15 to about 30; Q is a hydrophobic quaternizing unit selected from the group consisting of $C_8$–$C_{30}$ linear or branched alkyl, $C_6$–$C_{30}$ cycloalkyl, $C_7$–$C_{30}$ substituted or unsubstituted alkylenearyl, and mixtures thereof; X is an anion present in sufficient amount to provide electronic neutrality; n is from 0 to 3; and b) the balance carriers and adjunct ingredients.

The present invention also relates to a method for cleaning fabric, said method comprising the step of contacting an article of manufacture comprising fabric, preferably clothing, with an aqueous solution of a laundry detergent composition comprising a hydrophobically modified polyamine of the present invention.

These and other objects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to hydrophobically modified quaternized polyamines which are suitable for use in laundry detergent compositions. The hydrophobically modified polyamines of the present invention provide enhanced body soil and perspiration soil removal benefits.

It has been surprisingly discovered that hydrophobically modified quaternized polyamines have increased effectiveness when treating fabric which is soiled with human body oils, perspiration, etc. Without wishing to be limited by theory, the hydrophobically modified quaternary polyamines of the present invention have an unexpected balance of properties which makes the compounds amenable to penetrating fabric to solublize greasy, oily stains, while maintaining water solubility, and preserving the particulate soil suspension properties needed to direct the dirt away from the fabric thereby avoiding re-deposition. In one preferred embodiment of the present invention, the hydrophobically modified polyamines are used to formulate cleaning composition comprising nil surfactants. In addition, the hydrophobically modified polyamines of the present invention reinforce the cleaning actions of high suds and high phosphate cleaning systems.

The hydrophobically modified polyamines of the present invention do not aggregate onto the surface of fabric, whereas surfactants have a propensity to aggregate in this manner. Because the polyamines of the present invention do not form micelles there is no inter facial tension. This is particularly important with regard to the air/water interface where foam is formed. Therefore, low foaming can be achieved in the absence of foam reduction adjunct ingredients.

The polyamines of the present invention, in the absence of surfactants, has a surprising effect against surfactant sensitive soils which affect fabric, inter alia, dingy soils, grease, and oil.

When present in laundry detergent compositions, the polyamines are effective in an amount from about 0.01%, preferably from about 0.1%, more preferably from about 1%, most preferably from about 3% to about 50%, preferably to about 20%, more preferably to about 10%, most preferably to about 7% by weight, of said laundry detergent composition.

Hydrophobically Modified Quaternized Polyamines

For the purposes of the present invention the term "hydrophobically modified" is defined herein as the "reaction of a linear polyamine comprising from 2 to 5 nitrogens wherein each nitrogen has its backbone hydrogens replaced by a polyalkyleneoxy unit comprising at least about 15 alkyleneoxy units, with at least one equivalent per nitrogen of a quaternizing agent, said quaternizing agents comprising a linear alkyl moiety having at least 8 carbon atoms, a cyclic alkyl moiety having at least 6 carbon atoms, an alkylenearyl unit, inter alia, benzyl, having at least 7 carbon atoms, or mixtures thereof".

A "polyamine" for the purposes of the present invention is "an amine having less than 6 backbone nitrogen atoms and no branching", whereas for the purposes of the present invention, amines comprising more than 5 nitrogens are defined as "oligomeric amines" (oligoamines) or "polymeric amines" (polyalkyleneamines or polyalkyleneimines).

The hydrophobically modified polyamines of the present invention have the formula:

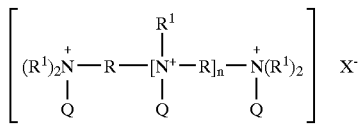

wherein R is $C_6$–$C_{20}$ linear or branched alkylene, and mixtures thereof; preferably $C_6$–$C_{12}$ linear alkylene, more preferably $C_6$–$C_8$ linear alkylene, most preferred backbone unit R is hexylene.

$R^1$ is an alkyleneoxy unit having the formula:

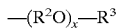

wherein $R^2$ is $C_2$–$C_4$ linear or branched alkylene, and mixtures thereof. Preferably $R^2$ comprises ethylene, 1,2-propylene, and mixtures thereof, preferably each $R^2$ unit is an ethylene unit. One embodiment of the present invention which provides advantages in a bleach comprising composition relates to hydrophobically modified zwitterionic polyamines comprising the first 1–6, preferably the first 1—3 of alkyleneoxy units as 1,2-propyleneoxy units followed by the balance ethyleneoxy units.

$R^3$ is hydrogen, $C_1$–$C_{22}$ alkyl, $C_7$–$C_{22}$ alkylenearyl, and mixtures thereof. $R^3$ is preferably hydrogen, $C_1$–$C_4$ alkyl, benzyl, and mixtures thereof; more preferably hydrogen.

The index x which describes the average number of alkyleneoxy units attached to the backbone nitrogen is from about 15 to about 30, preferably from 15 to 25, more preferably from 18 to 23, most preferred average value of alkyleneoxy units is 20. The formulator will recognize that when ethoxylating a polyamine, only an average number or statistical distribution of alkyleneoxy units will be know. Therefore, depending upon how "tightly" or how "exactly" a polyamine is alkoxylated, the average value may vary from embodiment to embodiment.

Each Q is independently $C_8$–$C_{30}$ linear or branched alkyl, $C_6$–$C_{30}$ cycloalkyl, $C_7$–$C_{30}$ substituted or unsubstituted alkylenearyl, and mixtures thereof; preferably Q is a hydrophobic quaternizing unit selected from the group consisting of C substituted or unsubstituted alkylenearyl, and mixtures thereof; more preferably benzyl, substituted benzyl, naphthyl, substituted naphthyl, and mixtures thereof. For the purposes of the present invention the formulae:

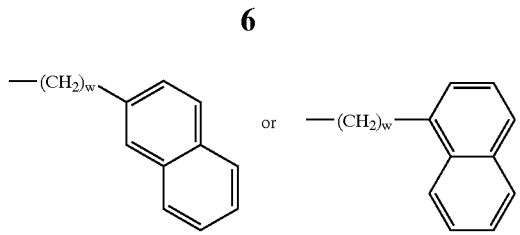

stands for the term "naphthyl" depending upon whether said unit comprises α-substitution or β-substitution. The index w has the value from 0 to 20. Other alkylene aryl units include besides benzyl, alkylenearyl units having the formula:

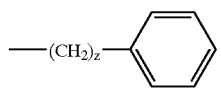

wherein the index z is from 1 to 24.

For the purposes of the present invention the term "substituted" as it applies to alkylenearyl units suitable as Q units, are one or more $C_1$–$C_{12}$ linear or branch alkyl moieties, provided the total number of carbon atoms including the aromatic ring does not exceed 30 carbon atoms.

A non-limiting example of a substitued alkylenearyl unit according to the present invention has the formula:

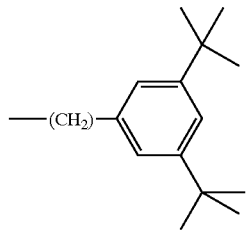

which is a 3,5-di-tert-butyl benzyl moiety.

The index n represents the number of secondary nitrogens in the backbone. The index n has the value from 0 to 3, preferably from 0 to 2, more preferably 1.

X is an anion present in sufficient amount to provide electronic neutrality. Non-limiting examples of anions are chlorine, bromine, iodine, methylsulfate, and mixtures thereof.

An example of a preferred hydrophobically modified polyamine according to the present invention has the formula:

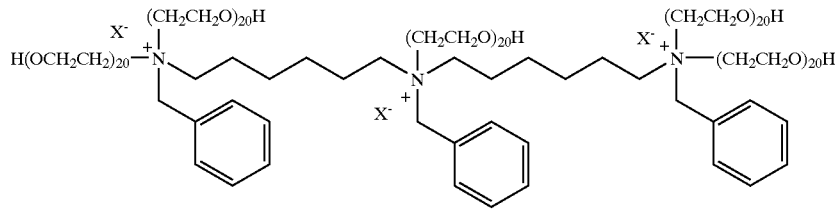

wherein X is a water soluble anion selected from the group consisting of chlorine, bromine, iodine, methylsulfate, and mixtures thereof.

Surfactant System

The laundry detergent compositions of the present invention comprise from about 0.01%, preferably from about 1%, more preferably from about 5%, most preferably from 10% to about 80%, preferably to about 50%, more preferably to about 30%, by weight of a surfactant system, said surfactant system comprising one or more surfactants selected from:

i) from 0%, preferably from about 0.01% to 100%, preferbably to 80% by weight, of one or more anionic surfactants;
ii) from 0%, preferably from about 0.01% to 100%, preferbably to 80% by weight, of one or more nonionic surfactants;
iii) optionally from 0.1% to about 80% by weight, of one or more cationic surfactants;
iv) optionally from 0.1% to about 80% by weight, of one or more zwinerionic surfactants;
v) optionally from 0.1% to about 80% by weight, of one or more ampholytic surfactants; or
vi) mixtures thereof.

A preferred surfactant system according to the present invention comprises from about 0.01% by weight, of one or more surfactants selected from:

i) from 1% to about 100% by weight, of an anionic surfactant selected from:
   a) linear alkyl benzene sulfonates;
   b) mid-chain branched aryl sulfonate surfactants having the formula:

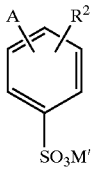

wherein A is a mid-chain branched alkyl unit having the formula:

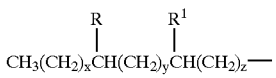

wherein R and $R^1$ are each independently hydrogen, $C_1$–$C_3$ alkyl, and mixtures thereof, provided the total number of carbon atoms in said alkyl unit is from 6 to 18 and at least one of R and $R^1$ is not hydrogen; x is an integer from 0 to 13; y is an integer from 0 to 13; z is 0 or 1; $R^2$ is hydrogen, $C_1$–$C_3$ alkyl, and mixtures thereof; M' is a water soluble cation with sufficient charge to provide neutrality;
   c) branched alkyl sulfate surfactants having the formula:

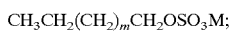

or the formula:

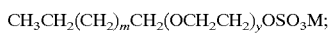

d) mid-chain branched alkyl sulfate surfactants having the formula:

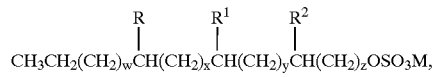

or the formula:

wherein R, $R^1$, and $R^2$ are each independently hydrogen, $C_1$–$C_3$ alkyl, and mixtures thereof, provided the total number of carbon atoms in said surfactant is from 14 to 20 and at least one of R, $R^1$, and $R^2$ is not hydrogen; the index w is an integer from 0 to 13; x is an integer from 0 to 13; y is an integer from 0 to 13; z is an integer of at least 1; provided w+x+y+z is from 8 to 14 and the total number of carbon atoms in a surfactant is from 14 to 20; $R^3$ is ethylene, 1,2-propylene, 1,3-propylene, 1,2-butylene, 1,4-butylene, and mixtures thereof; the average value of the index m is at least about 0.01; M is a water soluble cation of sufficient charge to provide electronic neutrality;

ii) from 0% to 100% by weight, of one or more nonionic surfactants;
iii) optionally from 0.1% to about 80% by weight, of one or more cationic surfactants;
iv) optionally from 0.1% to about 80% by weight, of one or more zwitterionic surfactants;
v) optionally from 0.1% to about 80% by weight, of one or more ampholytic surfactants; or
vi) mixtures thereof.

Depending upon the embodiment of the present invention one or more categories of surfactants may be chosen by the formulator, however, at least one anionic or at least one nonionic surfactant must be present. Within each category of surfactant, more that one type of surfactant can be selected.

Nonlimiting examples of surfactants useful herein include:
a) $C_{11}$–$C_{18}$ alkyl benzene sulfonates (LAS);
b) $C_{10}$–$C_{20}$ primary, branched-chain and random alkyl sulfates (AS);
c) $C_{10}$–$C_{18}$ secondary (2,3) alkyl sulfates having the formula:

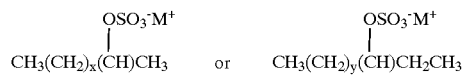

wherein x and (y+1) are integers of at least about 7, preferably at least about 9; said surfactants disclosed in U.S. Pat. No. 3,234,258 Morris, issued Feb. 8, 1966; U.S. Pat. No. 5,075,041 Lutz, issued Dec. 24, 1991; U.S. Pat. No. 5,349,101 Lutz et al., issued Sep. 20, 1994; and U.S. Pat. No. 5,389,277 Prieto, issued Feb. 14, 1995 each incorporated herein by reference;
d) $C_{10}$–$C_{18}$ alkyl alkoxy sulfates ($AE_xS$) wherein preferably x is from 1–7;
e) $C_{10}$–$C_{18}$ alkyl alkoxy carboxylates preferably comprising 1–5 ethoxy units;

f) $C_{12}$–$C_{18}$ alkyl ethoxylates, $C_6$–$C_{12}$ alkyl phenol alkoxylates wherein the alkoxylate units are a mixture of ethyleneoxy and propyleneoxy units, $C_{12}$–$C_{18}$ alcohol and $C_6$–$C_{12}$ alkyl phenol condensates with ethylene oxide/propylene oxide block polymers inter alia Pluronic® ex BASF which are disclosed in U.S. Pat. No. 3,929,678 Laughlin et al., issued Dec. 30, 1975, incorporated herein by reference;

g) Alkylpolysaccharides as disclosed in U.S. Pat. No. 4,565,647 Llenado, issued Jan. 26, 1986, incorporated herein by reference;

h) Polyhydroxy fatty acid amides having the formula:

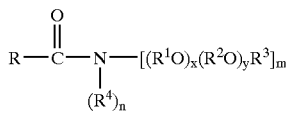

wherein R is $C_7$–$C_{21}$ linear alkyl, $C_7$–$C_{21}$ branched alkyl, $C_7$–$C_{21}$ linear alkenyl, $C_7$–$C_{21}$ branched alkenyl, and mixtures thereof.

$R^1$ is ethylene; $R^2$ is $C_3$–$C_4$ linear alkyl, $C_3$–$C_4$ branched alkyl, and mixtures thereof; preferably $R^2$ is 1,2-propylene. Nonionic surfactants which comprise a mixture of $R^1$ and $R^2$ units preferably comprise from about 4 to about 12 ethylene units in combination with from about 1 to about 4 1,2-propylene units. The units may be alternating, or grouped together in any combination suitable to the formulator. Preferably the ratio of $R^1$ units to $R^2$ units is from about 4:1 to about 8:1. Preferably an $R^2$ units (i.e. 1,2-propylene) is attached to the nitrogen atom followed by the balance of the chain comprising from 4 to 8 ethylene units.

$R^3$ is hydrogen, $C_1$–$C_4$ linear alkyl, $C_3$–$C_4$ branched alkyl, and mixtures thereof; preferably hydrogen or methyl, more preferably hydrogen.

$R^4$ is hydrogen, $C_1$–$C_4$ linear alkyl, $C_3$–$C_4$ branched alkyl, and mixtures thereof; preferably hydrogen. When the index m is equal to 2 the index n must be equal to 0 and the $R^4$ unit is absent and is instead replaced by a —[($R^1$O)$_x$($R^2$O)$_y$$R^3$] unit.

The index m is 1 or 2, the index n is 0 or 1, provided that when m is equal to 1, n is equal to 1; and when m is 2 n is 0; preferably m is equal to 1 and n is equal to one, resulting in one —[($R^1$O)$_x$($R^2$O)$_y$$R^3$] unit and $R^4$ being present on the nitrogen. The index x is from 0 to about 50, preferably from about 3 to about 25, more preferably from about 3 to about 10. The index y is from 0 to about 10, preferably 0, however when the index y is not equal to 0, y is from 1 to about 4. Preferably all of the alkyleneoxy units are ethyleneoxy units. Those skilled in the art of ethoxylated polyoxyalkylene alkyl amide surface active agents will recognized that the values for the indices x and y are average values and the true values may range over several values depending upon the process used to alkoxylate the amides.

Suitable means for preparing the polyoxyalkylene alkylamide surface active agents of the present invention can be found in "Surfactant Science Series", Editor Martin Schick, Volume 1, Chapter 8 (1967) and Volume XIX, Chapter 1 (1987) included herein by reference.

Mid-chain Branched Alkyl Sulfates

The surfactant systems of the present invention may comprise a mid-chain branched alkyl sulfate surfactant and/or a mid-chain branched alkyl alkoxy sulfate surfactant. Because mid-chain branched alkyl sulfate or alkyl alkoxy sulfate surfactants are not required when mid-chain branched aryl sulfonate surfactants are present, the surfactant system comprises from 0%, when present from 0.01%, preferably from about 0.1% more preferably from about 1% to about 100%, preferably to about 80% by weight, preferably to about 60%, most preferably to about 30% by weight, of the surfactant system. When the mid-chain branched alkyl sulfate surfactants or mid-chain branched alkyl alkoxy sulfate surfactants comprise 100% of the surfactant system said surfactants will comprise up to 60% by weight of the final laundry detergent composition.

The mid-chain branched alkyl sulfate surfactants of the present invention have the formula:

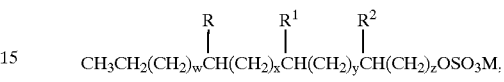

the alkyl alkoxy sulfates have the formula:

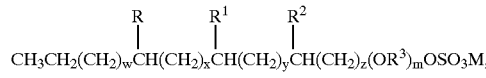

wherein R, $R^1$, and $R^2$ are each independently hydrogen, $C_1$–$C_3$ alkyl, and mixtures thereof; provided at least one of R, $R^1$, and $R^2$ is not hydrogen; preferably R, $R^1$, and $R^2$ are methyl; preferably one of R, $R^1$, and $R^2$ is methyl and the other units are hydrogen. The total number of carbon atoms in the mid-chain branched alkyl sulfate and alkyl alkoxy sulfate surfactants is from 14 to 20; the index w is an integer from 0 to 13; x is an integer from 0 to 13; y is an integer from 0 to 13; z is an integer of at least 1; provided w+x+y+z is from 8 to 14 and the total number of carbon atoms in a surfactant is from 14 to 20; $R^3$ is $C_1$–$C_4$ linear or branched alkylene, preferably ethylene, 1,2-propylene, 1,3-propylene, 1,2-butylene, 1,4-butylene, and mixtures thereof. However, a preferred embodiment of the present invention comprises from 1 to 3 units wherein $R^3$ is 1,2-propylene, 1,3-propylene, or mixtures thereof followed by the balance of the $R^3$ units comprising ethylene units. Another preferred embodiment comprises $R^3$ units which are randomly ethylene and 1,2-propylene units. The average value of the index m is at least about 0.01. When the index m has low values, the surfactant system comprises mostly alkyl sulfates with a small amount of alkyl alkoxy sulfate surfactant. Some tertiary carbon atoms may be present in the alkyl chain. however, this embodiment is not desired.

M denotes a cation, preferably hydrogen, a water soluble cation, and mixtures thereof. Non-limiting examples of water soluble cations include sodium, potassium, lithium, ammonium, alkyl ammonium, and mixtures thereof.

The preferred mid-chain branched alkyl sulfate and alkyl alkoxy sulfate surfactants of the present invention are "substantially linear" surfactants. The term "substantially linear" is defined for the purposes of the present invention as "alkyl units which comprise one branching unit or the chemical reaction products which comprise mixtures of linear (non-branched) alkyl units and alkyl units which comprise one branching unit". The term "chemical reaction products" refers to the admixture obtained by a process wherein substantially linear alkyl units are the desired product but nevertheless some non-branched alkyl units are formed. When this definition is taken together with preferably one of R, $R^1$, and $R^2$ is methyl and the other units are hydrogen, the preferred mid-chain branched alkyl sulfate and alkyl alkoxy sulfate surfactants comprise one methyl branch, preferably said methyl branch is not on the α, β, or the second to the last carbon atom. Typically the branched chains are a mixture of isomers.

The following illustrate preferred examples of mid-chain branched alkyl sulfate and alkoxy alkyl sulfate surfactants.

8-Methylundecyl sulfate:

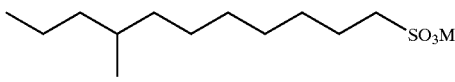

3-Methylundecyl sulfate:

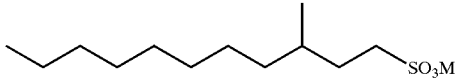

3-Methyltridecyl sulfate:

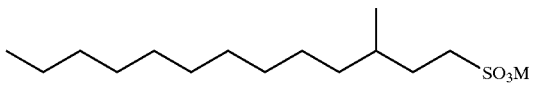

8-Methyltrdecyl sulfate:

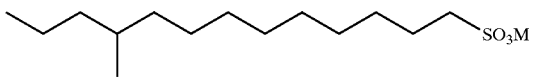

Mid-chain Branched Aryl Sulphonates

The surfactant systems of the present invention may comprise a mid-chain branched aryl sulphonate surfactant. Because mid-chain branched aryl sulfonate surfactants are not required when mid-chain branched alkyl sulfate and/or alkyl alkoxy surfactants are present, the surfactant system comprises from 0%, when present from 0.01%, preferably from about 0.1% more preferably from about 1% to about 100%, preferably to about 80% by weight, preferably to about 60%, most preferably to about 30% by weight, of the surfactant system. When the mid-chain branched aryl sulphonate surfactants comprise 100% of the surfactant system said mid-chain branched aryl sulphonate surfactants will comprise up to 60% by weight of the final laundry detergent composition.

The mid-chain branched aryl sulphonates of the present invention have the formula:

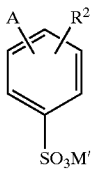

wherein A is a mid-chain branched alkyl unit having the formula:

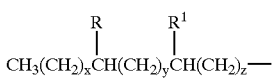

wherein R and R$^1$ are each independently hydrogen, C$_1$–C$_3$ alkyl, and mixtures thereof, provided at least one of R and R$^1$ is not hydrogen; preferably at least one R or R$^1$ is methyl; wherein the total number of carbon atoms in said alkyl unit is from 6 to 18. Some tertiary carbon atoms may be present in the alkyl chain, however, this embodiment is not desired.

The integer x is from 0 to 13. The integer y is from 0 to 13. The integer z is either 0 or 1, preferably 0.

R$^2$ is hydrogen, C$_1$–C$_3$ alkyl, and mixtures thereof. Preferably R$^2$ is hydrogen.

M' denotes a water soluble cation with sufficient charge to provide neutrality, preferably hydrogen, a water soluble cation, and mixtures thereof. Non-limiting examples of water soluble cations include sodium, potassium, lithium, ammonium, alkyl ammonium, and mixtures thereof.

The preferred mid-chain branched aryl sulphonate surfactants of the present invention are "substantially linear aryl" surfactants. The term "substantially linear aryl" is defined for the purposes of the present invention as "an alkyl unit which is taken together with an aryl unit wherein said alkyl unit preferably comprises one branching unit, however, a non-branched linear alkyl unit having an aryl unit bonded to the 2-carbon position as part of an admixture is included as a substantially linear aryl surfactant". The preferred alkyl units do not have a methyl branch on the second to the last carbon atom. Typically the branched chains are a mixture of isomers. However, in the case of the mid-chained branched aryl sulphonates of the present invention, the relative position of the aryl moiety is key to the functionality of the surfactant. Preferably the aryl moiety is attached to the second carbon atom in the branched chain as illustrated herein below.

The preferred mid-chain branched aryl sulphonates of the present invention will comprise a mixture of branched chains. Preferably R$^1$ is methyl, the index z is equal to 0, and the sulphate moiety is para (1,4) to the branched alkyl substituent thereby resulting in a "2-phenyl aryl sulphonate" defined herein by the general formula:

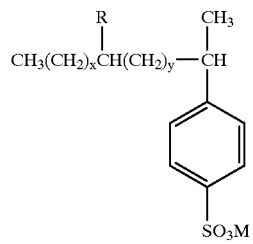

Typically 2-phenyl aryl sulphonates are formed as a mixture together with "3-phenyl aryl sulphonates" defined herein by the general formula:

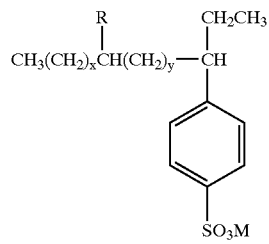

The surfactant properties of the mid-chain branched aryl sulphonates of the present invention can be modified by varying the ratio of 2-phenyl to 3-phenyl isomers in the final surfactant mixture. A convenient means for describing the relative amounts of isomers present is the "2/3 phenyl index" defined herein as "100 times the quotient of the amount of 2-phenyl isomer present divided by the amount of the 3-phenyl isomer which is present". Any convenient means, NMR, inter alia, can be used to determine the relative amounts of isomers present. A preferred 2/3 phenyl index is at least about 275 which corresponds to at least 2.75 times more 2-phenyl isomer present than the 3-phenyl isomer in the surfactant mixture. The preferred 2/3-phenyl index according to the present invention is from about 275, more preferably from about 350, most preferably from about 500 to about 10,000, preferably to about 1200, more preferably to about 700.

Those of ordinary skill in the art will recognize that the mid-chain branched surfactants of the present invention will be a mixture of isomers and the composition of the mixture will vary depending upon the process which is selected by the formulator to make the surfactants. For example, the following admixture is considered to comprise a substantially linear mid-chain branched aryl sulphonate admixture according to the present invention. Sodium para-(7-methylnonan-2-yl)benzenesulphonate, sodium para-(6-methylnonan-2-yl)benzenesulphonate, sodium para-(7-methylnonan-3-yl)benzene-sulphonate, sodium para-(7-methyldecan-2-yl)benzenesulphonate, sodium para-(7-methylnonanyl)benzenesulphonate.

Formulations

The compositions of the present invention may be in any form, inter alia, liquid, granular, paste. Depending upon the specific form of the laundry composition, as well as, the expected use thereof the formulator may will use different surfactant and adjunct ingredient combinations.

Preferably the Heavy Duty Granular compositions according to the present invention comprise:
a) from about 0.01%, preferably from about 0.1%, more preferably from 1% most preferably from 3% to about 20%, preferably to about 10%, more preferably to about 7% by weight, of a hydrophobically modified polyamine; and
b) from about 0.01% by weight, preferably from about 0.1% more preferably from about 1% to about 60%, preferably to about 30% by weight, of said composition, of a surfactant system, said surfactant system comprising:
  i) from 0.01%, preferably from about 0.1% more preferably from about 1% to about 100%, preferably to about 80% by weight, preferably to about 60%, most preferably to about 30% by weight, of a surfactant selected from the group consisting of alkyl sulfate surfactants, alkoxy sulfate surfactants, mid-chain branched alkyl sulfate surfactants, mid-chain branched alkoxy sulfate surfactants, mid-chain branched aryl sulfonate surfactants, and mixtures thereof;
  ii) optionally and preferably, from 0.01%, preferably from about 0.1% more preferably from about 1% to about 100%, preferably to about 80% by weight, preferably to about 60%, most preferably to about 30% by weight, of one or more anionic surfactants;
  iii) optionally, from 0.01%, preferably from about 0.1% more preferably from about 1% to about 100%, preferably to about 80% by weight, preferably to about 60%, most preferably to about 30% by weight, of one or more nonionic surfactants.

HDG laundry detergent compositions will typically comprise more of anionic detersive surfactants. Therefore, the formulator will employ a zwitterionic polyamine having a greater number of anionic units than the number of backbone cationic units. This net charge balance will ameliorate the negative interaction of the surfactant molecules with the hydrophilic soil active zwitterionic polymers.

By contrast, preferably the Heavy Duty Liquid (HDL) compositions according to the present invention comprise:
a) from about 0.01%, preferably from about 0.1%, more preferably from 1%, most preferably from 3% to about 20%, preferably to about 10%, more preferably to about 5% by weight, of a zwitterionic polyamine wherein said polyamine comprises less than or equal number of anionic substituents than the number of backbone quaternary nitrogen units; and
b) from about 0.01% by weight, preferably from about 0.1% more preferably from about 1% to about 60%, preferably to about 30% by weight, of said composition, of a surfactant system, said surfactant system comprising:
  i) from 0.01%, preferably from about 0.1% more preferably from about 1% to about 100%, preferably to about 80% by weight, preferably to about 60%, most preferably to about 30% by weight, of a surfactant selected from the group consisting of mid-chain branched alkyl sulfate surfactants, mid-chain branched alkoxy sulfate surfactants, mid-chain branched aryl sulfonate surfactants, and mixtures thereof;
  ii) preferably, from 0.01%, preferably from about 0.1% more preferably from about 1% to about 100%, preferably to about 80% by weight, preferably to about 60%, most preferably to about 30% by weight, of one or more nonionic surfactants, said nonionic surfactants selected form the group consisting of alcohols, alcohol ethoxylates, polyoxyalkylene alkylamides, and mixtures thereof;
  iii) optionally, from 0.01%, preferably from about 0.1% more preferably from about 1% to about 100%, preferably to about 80% by weight, preferably to about 60%, most preferably to about 30% by weight, of one or more nonionic surfactants.

HDL laundry detergent compositions will typically comprise more of a lesser amount of an anionic detersive surfactant and more nonionic surfactants. Therefore, the formulator will employ a zwitterionic polyamine having an equal number of anionic units as the number of cationic units or a greater number of cationic backbone units than the number of anionic units.

A preferred nil-surfactant Heavy Duty Granular composition according to the present invention comprises:
a) from about 0.01%, preferably from about 0.1%, more preferably from 1%, most preferably from 3% to about 20%, preferably to about 10%, more preferably to about 7% by weight, of a hydrophobically modified polyamine;
b) from about 1%, preferably from about 5%, more preferably from about 10% to about 80%, preferably to about 50%, more preferably to about 30% by weight, of detergent builder; and
c) the balance carriers and adjunct ingredients.

The nil surfactant formulations of the present invention can further comprise a bleaching system as described herein below. Nil-surfactant bleach containing compositions comprise:
a) from about 0.01%, preferably from about 0.1%, more preferably from 1%, most preferably from 3% to about 20%, preferably to about 10%, more preferably to about 7% by weight, of a hydrophobically modified polyamine;
b) from about 1%, preferably from 5% to about 80%, preferably to about 50% by weight, of the laundry detergent composition, a peroxygen bleaching system comprising:
  i) from about 40%, preferably from about 50%, more preferably from about 60% to about 100%, preferably to about 95%, more preferably to about 80% by weight, of the bleaching system, a source of hydrogen peroxide;
ii) optionally from about 0.1%, preferably from about 0.5% to about 60%, preferably to about 40% by weight, of the beaching system, a beach activator,
iii) optionally from about 1 ppb (0.0000001%), more preferably from about 100 ppb (0.00001%), yet more preferably from about 500 ppb (0.00005%), still more preferably from about 1 ppm (0.0001%) to about 99.9%, more preferably to about 50%, yet more preferably to about 5%, still more preferably to about 500 ppm (0.05%) by weight of the composition, of a transition-metal bleach catalyst;
iv) optionally from about 0.1% by weight, of a preformed peroxygen bleaching agent; and
c) the balance carriers and other adjunct ingredients.

A preferred nil-surfactant bleaching-contain composition according to the present invention is a composition comprising a transition metal bleach in the absence an added peroxygen bleach. As described herein above for surfactant containing compositions, sources of peroxygen bleaches include, but are not limited to, sources of hydrogen peroxide inter alia hydrogen peroxide, percarbonate, perborate. Alkali metal and alkaline earth metal percarbonate and perborate are typically found in laundry bleaching systems. These sources of hydrogen peroxide are typically formulated with one or more bleach activators inter alia nonanoyloxybenzenesulfonate (NOBS), tetraacetylethylenediamine (TAED). Bleach activators are typically viewed as precursors to the less stable but more reactive peroxyacid bleaching agents. Peroxyacids are formed in situ when the bleach activator (peroxyacid precursor) reacts with hydrogen peroxide or hydroperoxide anion via a perhydrolysis reaction:

a) from about 0.01%, preferably from about 0.1%, more preferably from 1%, most preferably from 3% to about 20%, preferably to about 10%, more preferably to about 7% by weight, of a hydrophobically modified polyamine;
b) from about 1 ppb (0.0000001%), more preferably from about 100 ppb (0.00001%), yet more preferably from about 500 ppb (0.00005%), still more preferably from about 1 ppm (0.0001%) to about 99.9%, more preferably to about 50%, yet more preferably to about 5%, still more preferably to about 500 ppm (0.05%) by weight of the composition, of a transition-metal bleach catalyst; preferably a bleach catalyst selected from the group consisting of 5,12-dimethyl -1,5,8,12-tertazabicyclo[6.6.2]-hexadecane, 5-ethyl-12-methyl-1,5,8, 12-tertaaza -bicyclo[6.6.2]hexadecane, 5,12-diethyl-1, 5,8,12-tertaaza -bicyclo[6.6.2]hexadecane, and mixtures thereof;
c) from about 1%, preferably from about 5%, more preferably from about 10% to about 80%, preferably to about 50%, more preferably to about 30% by weight, of detergent builder, and
d) the balance carriers and other adjunct ingredients wherein said composition does not comprise a source of peroxygen.

A further preferred nil surfactant formulation according to the present invention comprises one or more enzymes in combination with the hydrophobically modified polyamines of the present invention. An example of an enzyme comprising composition comprises:

a) from about 0.01%, preferably from about 0.1%, more preferably from 1%, most preferably from 3% to about 20%, preferably to about 10%, more preferably to about 7% by weight, of a hydrophobically modified polyamine;
b) from 0.0001%, more preferably from 0.0005%, most preferably from 0.001% to 2%, preferably to 0.1%, more preferably to 0.02% by weight, of pure enzyme; and
c) the balance carriers and other adjunct ingredients.

An example of a formulation which is suitable as a nil-surfactant laundry composition comprises:

a) from about 0.01%, preferably from about 0.1%, more preferably from 1%, most preferably from 3% to about 20%, preferably to about 10%, more preferably to about 7% by weight, of a hydrophobically modified polyamine;
b) from 0.0001%, more preferably from 0.0005%, most preferably from 0.001% to 2%, preferably to 0.1%, more preferably to 0.02% by weight, of pure enzyme; and
c) from about 1%, preferably from about 5%, more preferably from about 10% to about 80%, preferably to about 50%, more preferably to about 30% by weight, of detergent builder, and
d) from about 1%, preferably from about 5% to about 80%, preferably to about 50% by weight, of the laundry detergent composition, a peroxygen bleaching system comprising:
  i) from about 40%, preferably from about 50%, more preferably from about 60% to about 100%, preferably to about 95%, more preferably to about 80% by weight, of the bleaching system, a source of hydrogen peroxide;
  ii) optionally from about 0.1%, preferably from about 0.5% to about 60%, preferably to about 40% by weight, of the beaching system, a beach activator,
  iii) optionally from about 1 ppb (0.0000001%), more preferably from about 100 ppb (0.00001%), yet more preferably from about 500 ppb (0.00005%), still more preferably from about 1 ppm (0.0001%) to about 99.9%, more preferably to about 50%, yet more preferably to about 5%, still more preferably to about 500 ppm (0.05%) by weight of the composition, of a transition-metal bleach catalyst;
  iv) optionally from about 0.1% by weight, of a preformed peroxygen bleaching agent; and
c) the balance carriers and other adjunct ingredient, said adjunct ingredients are selected from the group consisting of dye transfer inhibiting agents, scum dispersants, suds suppressors, optical brighteners, whitening agents, dye fixing agents, light fading protection agents, dispersants, dyes, pigments, colorants, perfumes, germicides, and mixtures thereof.

Bleaching System

The hydrophobically modified polyamine-comprising laundry detergent compositions of the present invention may optionally comprise a bleaching system. Bleaching systems typically comprise a "bleaching agent" (source of hydrogen peroxide) and an "initiator" or "catalyst".

Preferred laundry detergent compositions of the present invention which comprise a bleaching system, comprise:

a) from about 0.01% by weight, of a hydrophobically modified polyamine according to the present invention;
b) from about 0.01% by weight, of a surfactant system comprising:

i) from 0% to 100% by weight, of the surfactant system one or more anionic surfactants;
ii) from 0% to 100% by weight, of the surfactant system one or more nonionic surfactants;
iii) optionally from 0.1% to about 80% by weight, of the surfactant system one or more cationic surfactants;
iv) optionally from 0.1% to about 80% by weight, of the surfactant system one or more zwitterionic surfactants;
v) optionally from 0.1% to about 80% by weight, of the surfactant system one or more ampholytic surfactants; or
vi) mixtures thereof;

c) from about 1%, preferably from about 5% to about 80%, preferably to about 50% by weight, of the laundry detergent composition, a peroxygen bleaching system comprising:
i) from about 40%, preferably from about 50%, more preferably from about 60% to about 100%, preferably to about 95%, more preferably to about 80% by weight, of the bleaching system, a source of hydrogen peroxide;
ii) optionally from about 0.1%, preferably from about 0.5% to about 60%, preferably to about 40% by weight, of the beaching system, a beach activator;
iii) optionally from about 1 ppb (0.0000001%), more preferably from about 100 ppb (0.00001%), yet more preferably from about 500 ppb (0.00005%), still more preferably from about 1 ppm (0.0001%) to about 99.9%, more preferably to about 50%, yet more preferably to about 5%, still more preferably to about 500 ppm (0.05%) by weight of the composition, of a transition-metal bleach catalyst;
iv) optionally from about 0.1% by weight, of a preformed peroxygen bleaching agent; and d) the balance carriers and other adjunct ingredients.

Bleaching Agents

Hydrogen peroxide sources are described in detail in the herein incorporated Kirk Othmer's Encyclopedia of Chemical Technology, 4th Ed (1992, John Wiley & Sons), Vol. 4, pp. 271–300 "Bleaching Agents (Survey)", and include the various forms of sodium perborate and sodium percarbonate, including various coated and modified forms.

Sources of hydrogen peroxide which are suitable for use in the compositions of the present invention include, but are not limited to, perborates, percarbonates, perphosphates, persulfates, and mixtures thereof. Preferred sources of hydrogen peroxide are sodium perborate monohydrate, sodium perborate tetrahydrate, sodium percarbonate and sodium persulfate, more preferably are sodium perborate monohydrate, sodium perborate tetrahydrate, and sodium percarbonate. When present the source of hydrogen peroxide is present at a level of from about 40%, preferably from about 50%, more preferably from about 60% to about 100%, preferably to about 95%, more preferably to about 80% by weight, of the bleaching system. Embodiments which are bleach comprising pre-soak compositions may comprise from 5% to 99% of the source of hydrogen peroxide.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with a silicate, borate or water-soluble surfactants.

Bleach Activators

Preferably, the source of hydrogen peroxide (peroxygen bleach component) in the composition is formulated with an activator (peracid precursor). The activator is present at levels of from about 0.01%, preferably from about 0.5%, more preferably from about 1% to about 15%, preferably to about 10%, more preferably to about 8%, by weight of the composition. Also, bleach activators will comprise from about 0.1% to about 60% by weight, of the beaching system When the herein described bleaching system comprises 60% by weight, of an activator (the maximal amount) and said composition (bleaching composition, laundry detergent, or otherwise) comprises 15% by weight of said activator (the maximal amount by weight), said composition will comprise 25% by weight of a bleaching system (60% of which is bleach activator, 40% a source of hydrogen peroxide). However, this is not meant to restrict the formulator to a 60:40 ratio of activator to hydrogen peroxide source.

Preferably the mole ratio of peroxygen bleaching compound (as AvO) to bleach activator in the present invention generally ranges from at least 1:1, preferably from about 20:1, more preferably from about 10:1 to about 1:1, preferably to about 3:1.

Preferred activators are selected from the group consisting of tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, most preferably benzoylcaprolactam and benzoylvalerolactam. Particularly preferred bleach activators in the pH range from about 8 to about 9.5 are those selected having an OBS or VL leaving group.

Preferred hydrophobic bleach activators include, but are not limited to, nonanoyloxybenzenesulphonate (NOBS), 4-[N-(nonaoyl) amino hexanoyloxy]-benzene sulfonate sodium salt (NACA-OBS) an example of which is described in U.S. Pat. No. 5,523,434, decanoyloxybenzenesulphonate (LOBS or $C_{12}$-OBS), 10-undecenoyloxybenzenesulfonate (UDOBS or $C_{11}$-OBS with unsaturation in the 10 position), and decanoyloxybenzoic acid (DOBA).

Preferred bleach activators are those described in U.S. Pat. No. 5,698,504 Christie et al., issued Dec. 16, 1997; U.S. Pat. No. 5,695,679 Christie et al. issued Dec. 9, 1997; U.S. Pat. No. 5,686,401 Willey et al., issued Nov. 11, 1997; U.S. Pat. No. 5,686,014 Hartsborn et al., issued Nov. 11, 1997; U.S. Pat. No. 5,405,412 Willey et al., issued Apr. 11, 1995; U.S. Pat. No. 5,405,413 Willey al., issued Apr. 11, 1995; U.S. Pat. No. 5,130,045 Mitchel et al., issued Jul. 14, 1992; and U.S. Pat. No. 4,412,934 Chung et al., issued Nov. 1, 1983, and U.S. Pat. No. 5,998,350 and WO 94/28104; acyl lactam activators, as described in U.S. Pat. Nos. 5,698,504, 5,695,679 and 5,686,014, each of which is cited herein above, are very useful herein, especially the acyl caprolactams (see for example WO 94-28102 A) and acyl valerolactams, U.S. Pat. No. 5,503,639 Willey et al., issued Apr. 2, 1996 all of which are incorporated herein by reference.

Quaternary substituted bleach activators may also be included. The present cleaning compositions preferably comprise a quaternary substituted bleach activator (QSBA) or a quaternary substituted peracid (QSP); more preferably, the former. Preferred QSBA structures are further described in U.S. Pat. No. 5,686,015 Willey et al., issued Nov. 11, 1997; U.S. Pat. No. 5,654,421 Taylor et al., issued Aug. 5, 1997; U.S. Pat. No. 5,460,747 Gosselink et al., issued Oct. 24, 1995; U.S. Pat. No. 5,584,888 Miracle et al., issued Dec. 17, 1996; and U.S. Pat. No. 5,578,136 Taylor et al., issued Nov. 26, 1996; all of which are incorporated herein by reference.

Highly preferred bleach activators useful herein are amide-substituted as described in U.S. Pat. Nos. 5,698,504, 5,695,679, and U.S. Pat. No. 5,686,014 each of which are cited herein above. Preferred examples of such bleach activators include: (6-octanamidocaproyl) oxybenzenesulfonate, (6-nonanamidocaproyl) oxybenzenesulfonate, (6-decanamidocaproyl) oxybenzenesulfonate and mixtures thereof.

Other useful activators, disclosed in U.S. Pat. Nos. 5,698,504, 5,695,679, 5,686,014 each of which is cited herein above and U.S. Pat. No. 4,966,723 Hodge et al., issued Oct. 30, 1990, include benzoxazin-type activators, such as a $C_6H_4$ ring to which is fused in the 1,2-positions a moiety —C(O)OC($R^1$)=N—.

Depending on the activator and precise application, good bleaching results can be obtained from bleaching systems having with in-use pH of from about 6 to about 13, preferably from about 9.0 to about 10.5. Typically, for example, activators with electron-withdrawing moieties are used for near-neutral or sub-neutral pH ranges. Alkalis and buffering agents can be used to secure such pH.

Transition Metal Bleach Catalyst

The laundry detergent compositions of the present invention optionally comprises a bleaching system which contains one or more bleach catalysts. Selected bleach catalysts inter alia 5,12-dimethyl-1,5,8,12-tertaaza-bicyclo[6.6.2]hexadecane manganese (II) chloride may be formulated into bleaching systems which do not require a source of hydrogen peroxide or peroxygen bleach. The compositions comprise from about 1 ppb (0.0000001%), more preferably from about 100 ppb (0.00001%), yet more preferably from about 500 ppb (0.00005%), still more preferably from about 1 ppm (0.0001%) to about 99.9%, more preferably to about 50%, yet more preferably to about 5%, still more preferably to about 500 ppm (0.05%) by weight of the composition, of a transition-metal bleach catalyst Non-limiting examples of suitable manganese-based catalysts are disclosed in U.S. Pat. No. 5,576,282 Miracle et al., issued Nov. 19, 1996; U.S. Pat. No. 5,246,621 Favre et al., issued Sep. 21, 1993; U.S. Pat. No. 5,244,594 Favre et al., issued Sep. 14, 1993; U.S. Pat. No. 5,194,416 Jureller et al., issued Mar. 16, 1993; U.S. Pat. No. 5,114,606 van Vliet et al., issued May 19, 1992; U.S. Pat. No. 4,430,243 Bragg, issued Feb. 7, 1984; U.S. Pat. No. 5,114,611 van Kralingen, issued May 19, 1992; U.S. Pat. No. 4,728,455 Rerek, issued Mar. 1, 1988; U.S. Pat. No. 5,284,944 Madison, issued Feb. 8, 1994; U.S. Pat. No. 5,246,612 van Dijk et al., issued Sep. 21, 1993; U.S. Pat. No. 5,256,779 Kerschner et al., issued Oct. 26, 2993; U.S. Pat. No. 5,280,117 Kerschner et al., issued Jan. 18, 1994; U.S. Pat. No. 5,274,147 Kerschner et al., issued Dec. 28, 1993; U.S. Pat. No. 5,153,161 Kerschner et al., issued Oct. 6, 1992; and U.S. Pat. No. 5,227,084 Martens et al., issued Jul. 13, 1993; and European Pat. App. Pub. Nos. 549,271 A1, 549,272 A1, 544,440 A2, and 544,490 A1.

Non-limiting examples of suitable cobalt-based catalysts are disclosed in U.S. Pat. No. 5,597,936 Perkins et al., issued Jan. 28, 1997; U.S. Pat. No. 5,595,967 Miracle et al., issued Jan. 21, 1997; U.S. Pat. No. 5,703,030 Perkins et al., issued Dec. 30, 1997; U.S. Pat. No. 4,810,410 Diakun et al, issued Mar. 7, 1989; M. L. Tobe, "Base Hydrolysis of Transition-Metal Complexes", Adv. Inorg. Bioinorg. Mech., (1983), 2, pages 1–94; J. Chem. Ed. (1989), 66 (12), 1043–45; The Synthesis and Characterization of Inorganic Compounds, W. L. Jolly (Prentice-Hall; 1970), pp. 461–3; Inorg. Chem., 18, 1497–1502 (1979); Inorg. Chem., 21, 2881–2885 (1982); Inorg. Chem., 18, 2023–2025 (1979); Inorg. Synthesis, 173–176 (1960); and Journal of physical Chemistry, 56, 22–25 (1952).

Further examples of preferred macrocyclic ligand comprising bleach catalysts are described in WO 98/39406 A1 published Sep. 11, 1998 and included herein by reference. Suitable examples of these bleach catalysts include:

Dichloro-5,12-dimethyl-1,5,8,12-tetraazabicyclo[6.6.2]hexadecane maganese(II)

Diaquo-5,12-dimethyl-1,5,8,12-tetraazabicyclo[6.6.2]hexadecane manganese(II) hexafluorophosphate Aquo-hydroxy-5,12-dimethyl-1,5,8,12-tetraazabicyclo[6.6.2]hexadecane manganese(III) hexafluorophosphate Diaquo-5,12-dimethyl-1,5,8,12-tetraazabicyclo[6.6.2]hexadecane manganese(II) tetrafluoroborate Dichloro-5,12-dimethyl-1,5,8,12-tetraazabicyclo[6.6.2]hexadecane manganese(III) hexafluorophosphate Dichloro-5,12-di-n-butyl-1,5,8,12-tetraazabicyclo[6.6.2]hexadecane manganese(II)

Dichloro-5,12-dibenzyl-1,5,8,12-tetrabicyclo[6.6.2]hexadecane manganese(II)

Dichloro-5-n-butyl-12-methyl-1,5,8,12-tetraaza-bicyclo[6.6.2]hexadecane manganese(II)

Dichloro-5-n-octyl-12-methyl-1,5,8,12-tetraaza-bicyclo[6.6.2]hexadecane manganese(II)

Dichloro-5-n-butyl-12-methyl-1,5,8,12-tetraaza-bicyclo[6.6.2]hexadecane manganese(II).

Pre-formed Bleaching Agents

The bleaching systems of the present invention may optionally further comprise from 0.1%, preferably from 1%, more preferably from 5% to about 10%, preferably to about 7% by weight, of one or more pre-formed bleaching agents. Pre-formed bleaching materials typically have the general formula:

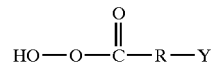

wherein R is a $C_1$–$C_{22}$ alkylene, $C_1$–$C_{22}$ substituted alkylene, phenylene, $C_6$–$C_{23}$ substituted phenylene, and mixtures thereof, Y is hydrogen, halogen, alkyl, aryl, —C(O)OH, —C(O)OOH, and mixtures thereof.

The organic percarboxylic acids usable in the present invention can contain either one or two peroxy groups and can be either aliphatic or aromatic. When the organic percarboxylic acid is aliphatic, the unsubstituted acid has the general formula:

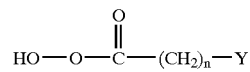

wherein Y can be hydrogen, methyl, methyl chloride, carboxylate, percarboxylate; and n is an integer having the value from 1 to 20.

When the organic percarboxylic acid is aromatic, the unsubstituted acid has the general formula:

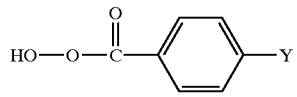

wherein Y can be hydrogen, alkyl, haloalkyl, carboxylate, percarboxylate, and mixtures thereof Typical monoperoxy percarboxylic acids useful herein include alkyl percarboxylic acids and aryl percarboxylic acids such as:
 i) peroxybenzoic acid and ring-substituted peroxybenzoic acids, e.g., peroxy-o-naphthoic acid;
 ii) aliphatic, substituted aliphatic and arylalkyl monoperoxy acids, e.g. peroxylauric acid, peroxystearic acid, and N,N-phthaloylaminoperoxycaproic acid (PAP).

Typical diperoxy percarboxylic acids useful herein include alkyl diperoxy acids and aryldiperoxy acids, such as:
 iii) 1,12-diperoxydodecanedioic acid;
 iv) 1,9-diperoxyazelaic acid;
 v) diperoxybrassylic acid; diperoxysebacic acid and diperoxyisophthalic acid;
 vi) 2-decyldiperoxybutane-1,4-dioic acid;
 vii) 4,4'-sulfonybisperoxybenzoic acid.

A non-limiting example of a highly preferred pre-formed bleach includes 6-nonylamino-6-oxoperoxycaproic acid (NAPAA) as described in U.S. Pat. No. 4,634,551 Burns et al., issued Jan. 6, 1987 included herein by reference.

As well as the herein described peroxygen bleaching compositions, the compositions of the present invention may also comprise as the bleaching agent a chlorine-type bleaching material. Such agents are well known in the art, and include for example sodium dichloroisocyanurate ("NaDCC"). However, chlorine-type bleaches are less preferred for compositions which comprise enzymes.

Enzymes

The term "enzyme" or "detersive enzyme", as used herein, means any enzyme having a cleaning, stain removing or otherwise beneficial effect in a laundry, hard surface cleaning, or other cleaning formulation or composition as described herein. In general, enzymes are present in the compositions of the present invention at a level of from 0.0001%, more preferably from 0.0005%. most preferably from 0.001% to 2%, preferably to 0.1%, more preferably to 0.02% by weight, of pure enzyme. Preferred enzymes are hydrolases such as proteases, amylases and lipases. Preferred enzymes for liquid laundry purposes include, but are not limited to, inter alia proteases, cellulases, lipases and peroxidases.

Protease Enzymes

The preferred liquid laundry detergent compositions according to the present invention further comprise at least 0.001% by weight, of a protease enzyme. However, an effective amount of protease enzyme is sufficient for use in the liquid laundry detergent compositions described herein. The term "an effective amount" refers to any amount capable of producing a cleaning, stain removal, soil removal, whitening, deodorizing, or freshness improving effect on substrates such as fabrics. In practical terms for current commercial preparations, typical amounts are up to about 5 mg by weight, more typically 0.01 mg to 3 mg, of active enzyme per gram of the detergent composition. Stated otherwise, the compositions herein will typically comprise from 0.001% to 5%, preferably 0.01%–1% by weight of a commercial enzyme preparation. The protease enzymes of the present invention are usually present in such commercial preparations at levels sufficient to provide from 0.005 to 0.1 Anson units (AU) of activity per gram of composition.

Preferred liquid laundry detergent compositions of the present invention comprise modified protease enzymes derived from *Bacillus amyloliguefaciens* or *Bacillus lentus*. For the purposes of the present invention, protease enzymes derived from *B. amyloliquefaciens* are further referred to as "subtilisin BPN'" also referred to as "Protease A" and protease enzymes derived from *B. Lentus* are further referred to as "subtilisin 309". For the purposes of the present invention, the numbering of *Bacillus amyloliquefaciens* subtilisin, as described in the patent applications of A. Baeck, et al, entitled "Protease-Containing Cleaning Compositions" having U.S. Ser. No. 08/322,676, serves as the amino acid sequence numbering system for both subtilisin BPN' and subtilisin 309.

Derivatives of *Bacillus amyloliguefaciens* subtilisin -BPN' enzymes

A preferred protease enzyme for use in the present invention is a variant of Protease A (BPN') which is a non-naturally occurring carbonyl hydrolase variant having a different proteolytic activity, stability, substrate specificity, pH profile and/or performance characteristic as compared to the precursor carbonyl hydrolase from which the amino acid sequence of the variant is derived. This variant of BPN' is disclosed in EP 130,756 A, Jan. 9, 1985.

Protease B

A preferred protease enzyme for use in the present invention is Protease B. Protease B is a non-naturally occurring carbonyl hydrolase variant having a different proteolytic activity, stability, substrate specificity, pH profile and/or performance characteristic as compared to the precursor carbonyl hydrolase from which the amino acid sequence of the variant is derived Protease B is a variant of BPN' in which tyrosine is replaced with leucine at position +217 and as further disclosed in EP 303,761 A, Apr. 28, 1987 and EP 130,756 A, Jan. 9, 1985.

Protease C

A preferred protease enzyme for use in the compositions of the present invention Protease C. Protease C is a variant of an alkaline serine protease from *Bacillus* in which lysine replaced arginine at position 27, tyrosine replaced valine at position 104, serine replaced asparagine at position 123, and alanine replaced threonine at position 274. Protease C is described in EP 90915958:4, corresponding to WO 91/06637, Published May 16, 1991. Genetically modified variants, particularly of Protease C, are also included herein.

Protease D

A preferred protease enzyme for use in the present invention is Protease D. Protease D is a carbonyl hydrolase variant derived from *Bacillus lentus* subtilisin as described in WO 95/10615 published Apr. 20, 1995 by Genencor International.

A further preferred protease enzyme for use in combination with the modified polyamines of the present invention is ALCALASE® from Novo. Another suitable protease is obtained from a strain of *Bacillus*, having maximum activity throughout the pH range of 8–12, developed and sold as ESPERASE® by Novo Industries A/S of Denmark, hereinafter "Novo". The preparation of this enzyme and analogous enzymes is described in GB 1,243,784 to Novo. Other suitable proteases include SAVINASE® from Novo and MAXATASE® from International Bio-Synthetics, Inc., The Netherlands. See also a high pH protease from *Bacillus* sp. NCIMB 40338 described in WO 9318140 A to Novo. Enzymatic detergents comprising protease, one or more other enzymes, and a reversible protease inhibitor are described in WO 9203529 A to Novo. Other preferred proteases include those of WO 9510591 A to Procter & Gamble. When desired, a protease having decreased adsorption and increased hydrolysis is available as described in WO 9507791 to Procter & Gamble. A recombinant trypsin-like protease for detergents suitable herein is described in WO 9425583 to Novo.

Other particularly useful proteases are described in WO 99/20727, WO 99/20726, and WO 99/20723 all filed on Oct. 23, 1998 from The Procter & Gamble Company.

Also suitable for the present invention are proteases described in patent applications EP 251 446 and WO 91/06637, protease BLAP® described in WO91/02792 and their variants described in WO 95/23221.

See also a high pH protease from *Bacillus* sp. NCIMB 40338 described in WO 93/18140 A to Novo. Enzymatic detergents comprising protease, one or more other enzymes, and a reversible protease inhibitor are described in WO 92/03529 A to Novo. When desired, a protease having decreased adsorption and increased hydrolysis is available as described in WO 95/07791 to Procter & Gamble. A recombinant trypsin-like protease for detergents suitable herein is described in WO 94/25583 to Novo. Other suitable proteases are described in EP 516 200 by Unilever.

Commercially available proteases useful in the present invention are known as ESPERASE®, ALCALASE®, DURAZYM®, SAVINASE®, EVERLASE® and KANNASE® all from Novo Nordisk A/S of Denmark, and as MAXATASE®, MAXACAL®, PROPERASE® and MAX-APEM® all from Genencor International (formerly Gist-Brocades of The Netherlands). A preferred protease for use in the present invention is the protease enzyme as described in WO99/20771 published Apr. 29, 1999.

In addition to the above-described protease enzymes, other enzymes suitable for use in the liquid laundry detergent compositions of the present invention are further described herein below.

Other Enzymes

Enzymes in addition to the protease enzyme can be included in the present detergent compositions for a variety of purposes, including removal of protein-based, carbohydrate-based, or triglyceride-based stains from surfaces such as textiles, for the prevention of refugee dye transfer, for example in laundering, and for fabric restoration. Suitable enzymes include amylases, lipases, cellulases, peroxidases, and mixtures thereof of any suitable origin, such as vegetable, animal, bacterial fungal and yeast origin. Preferred selections are influenced by factors such as pH-activity and/or stability optima, thermostability, and stability to active detergents, builders and the like. In this respect bacterial or fungal enzymes are preferred, such as bacterial amylases and proteases, and fungal cellulases.

Amylases suitable herein include, for example, α-amylases described in GB 1,296,839 to Novo; RAPIDASE®, International Bio-Synthetics, Inc. and TERMAMYL®, Novo. FUNGAMYL® from Novo is especially useful. Engineering of enzymes for improved stability, e.g., oxidative stability, is known. See, for example J. Biological Chem., Vol. 260, No. 11, Jun. 1985, pp 6518–6521 and WO 9402597 to Novo, Feb. 3, 1994, and WO 9509909 A to Novo.

Cellulases usable herein include both bacterial and fungal types, preferably having a pH optimum between 5 and 9.5. U.S. Pat. No. 4,435,307, Barbesgoard et al, Mar. 6, 1984, discloses suitable fungal cellulases from *Humicola insolens* or *Humicola* strain DSM1800 or a cellulose 212-producing fungus belonging to the genus *Aeromonas*, and cellulase extracted from the hepatopancreas of a marine mollusk, *Dolabella Auricula Solander*. Suitable cellulases are also disclosed in GB-A-2.075.028; GB-A-2.095.275 and DE-OS-2.247.832. CAREZYME® (Novo) is especially useful. See also WO 9117243 to Novo.

Suitable lipase enzymes for detergent usage include those produced by microorganisms of the *Pseudomonas* group, such as *Pseudomonas stutzeri* ATCC 19.154, as disclosed in GB 1,372,034. See also lipases in Japanese Patent Application 53,20487, laid open Feb. 24, 1978. This lipase is available from Amano Pharmaceutical Co. Ltd., Nagoya, Japan, under the trade name Lipase P "Amano," or "Amano-P." Other suitable commercial lipases include Amano-CES, lipases ex *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. LIPOLASE® enzyme derived from *Humicola lanuginosa* and commercially available from Novo, see also EP 341,947, is a preferred lipase for use herein. Lipase and amylase variants stabilized against peroxidase enzymes are described in WO 9414951 A to Novo. See also WO 9205249 and RD 94359044.

Cutinase enzymes suitable for use herein are described in WO 8809367 A to Genencor.

Peroxidase enzymes may be used in combination with oxygen sources, e.g., caronate, perborate, hydrogen peroxide, etc., for "solution bleaching" or prevention of transfer of dyes or pigments removed from substrates during the wash to other substrates present in the wash solution. Known peroxidases include horseradish peroxidase, ligninase, and haloperoxidases such as chloro- or bromo-peroxidase. Peroxidase-containing detergent compositions are disclosed in WO 89099813 A, Oct. 19, 1989 to Novo and WO 8909813 A to Novo.

A range of enzyme materials and means for their incorporation into synthetic detergent compositions is also disclosed in WO 9307263 A and WO 9307260 A to Genencor International, WO 8908694 A to Novo, and U.S. Pat. No. 3,553,139 McCarty et al., issued Jan. 5, 1971. Enzymes are further disclosed in U.S. Pat. No. 4,101,457 Place et al, issued Jul. 18, 1978, and U.S. Pat. No. 4,507,219 Hughes, issued Mar. 26, 1985. Enzyme materials useful for liquid detergent formulations, and their incorporation into such formulations, are disclosed in U.S. Pat. No. 4,261,868 Hora et al., issued Apr. 14, 1981. Enzymes for use herein can be stabilized by various techniques. Enzyme stabilization techniques are disclosed and exemplified in U.S. Pat. No. 3,600,319 Gedge et al., issued Aug. 17, 1971; EP 199,405 and EP 200,586, Oct. 29, 1986, Venegas. Enzyme stabilization systems are also described, for example, in U.S. Pat. No. 3,519,570. A useful *Bacillus*, sp. AC13 giving proteases, xylanases and cellulases, is described in WO 9401532 A to Novo.

Enzyme Stabilizing System

Enzyme-containing, including but not limited to, liquid compositions, herein may comprise from about 0.001%, preferably from about 0.005%, more preferably from about 0.01% to about 10%, preferably to about 8%, more preferably to about 6% by weight, of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

One stabilizing approach is the use of water-soluble sources of calcium and/or magnesium ions in the finished compositions which provide such ions to the enzymes. Calcium ions are generally more effective than magnesium ions and are preferred herein if only one type of cation is being used. Typical detergent compositions, especially liquids, will comprise from about 1 to about 30, preferably from about 2 to about 20, more preferably from about 8 to about 12 millimoles of calcium ion per liter of finished detergent composition, though variation is possible depending on factors including the multiplicity, type and levels of enzymes incorporated. Preferably water-soluble calcium or magnesium salts are employed, including for example calcium chloride, calcium hydroxide, calcium formate, calcium malate, calcium maleate, calcium hydroxide and calcium acetate; more generally, calcium sulfate or magnesium salts corresponding to the exemplified calcium salts may be used. Further increased levels of Calcium and/or Magnesium may of course be useful, for example for promoting the grease-cutting action of certain types of surfactant.

Another stabilizing approach is by use of borate species disclosed in U.S. Pat. No. 4,537,706 Severson, issued Aug. 27, 1985. Borate stabilizers, when used, may be at levels of up to 10% or more of the composition though more typically, levels of up to about 3% by weight of boric acid or other borate compounds such as borax or orthoborate are suitable for liquid detergent use. Substituted boric acids such as phenylboronic acid, butaneboronic acid, p-bromophenylboronic acid or the like can be used in place of boric acid and reduced levels of total boron in detergent compositions may be possible though the use of such substituted boron derivatives Stabilizing systems of certain cleaning compositions may further comprise from 0, preferably from about 0.01% to about 10%, preferably to about 6% by weight, of chlorine bleach scavengers, added to prevent chlorine bleach species present in many water supplies from attacking and inactivating the enzymes, especially under alkaline conditions. While chlorine levels in water may be small, typically in the range from about 0.5 ppm to about 1.75 ppm, the available chlorine in the total volume of water that comes in contact with the enzyme, for example during fabric-washing, can be relatively large; accordingly, enzyme stability to chlorine in-use is sometimes problematic. Since perborate or percarbonate, which have the ability to react with chlorine bleach, may present in certain of the instant compositions in amounts accounted for separately from the stabilizing system, the use of additional stabilizers against chlorine, may, most generally, not be essential, though improved results may be obtainable from their use. Suitable chlorine scavenger anions are widely known and readily available, and, if used, can be salts containing ammonium cations with sulfite, bisulfite, thiosulfite, thiosulfate, iodide, etc. Antioxidants such as carbamate, ascorbate, etc., organic amines such as ethylenediaminetetraacetic acid (EDTA) or alkali metal salt thereof, monoethanolamine (MEA), and mixtures thereof can likewise be used. Likewise, special enzyme inhibition systems can be incorporated such that different enzymes have maximum compatibility. Other conventional scavengers such as bisulfate, nitrate, chloride, sources of hydrogen peroxide such as sodium perborate tetrahydrate, sodium perborate monohydrate and sodium percarbonate, as well as phosphate, condensed phosphate, acetate, benzoate, citrate, formate, lactate, malate, tartrate, salicylate, etc., and mixtures thereof can be used if desired. In general, since the chlorine scavenger function can be performed by ingredients separately listed under better recognized functions, (e.g., hydrogen peroxide sources), there is no absolute requirement to add a separate chlorine scavenger unless a compound performing that function to the desired extent is absent from an enzyme-containing embodiment of the invention; even then, the scavenger is added only for optimum results. Moreover, the formulator will exercise a chemist's normal skill in avoiding the use of any enzyme scavenger or stabilizer which is majorly incompatible, as formulated, with other reactive ingredients, if used. In relation to the use of ammonium salts, such salts can be simply admixed with the detergent composition but are prone to adsorb water and/or liberate ammonia during storage. Accordingly, such materials, if present, are desirably protected in a particle such as that described in U.S. Pat. No. 4,652,392 Baginski et al., issued Mar. 24, 1987.

Adjunct Ingredients

The following are non-limiting examples of adjunct ingredients useful in the laundry compositions of the present invention, said adjunct ingredients include builders, optical brighteners, soil release polymers, dye transfer agents, dispersents, enzymes, suds suppressers dyes, perfumes, colorants, filler salts, hydrotropes, photoactivators, fluorescers fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

Builders

The laundry detergent compositions of the present invention preferably comprise one or more detergent builders or builder systems. When present, the compositions will typically comprise at least about 1% builder, preferably from about 5%, more preferably from about 10% to about 80%, preferably to about 50%, more preferably to about 30% by weight, of detergent builder.

The level of builder can vary widely depending upon the end use of the composition and its desired physical form. When present, the compositions will typically comprise at least about 1% builder. Formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839 Rieck, issued May 12, 1987. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2SiO_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

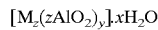

$$[M_z(zAlO_2)_y] \cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

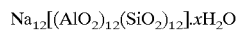

$$Na_{12}[(AlO_2)_{12}(SiO_2)_{12}] \cdot xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "poly-carboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in U.S. Pat. No. 3,128,287 Berg, issued Apr. 7, 1964, and U.S. Pat. No. 3,635,830 Lamberti et al., issued Jan. 18, 1972. See also "TMS/TDS" builders of U.S. Pat. No. 4,663,071 Bush et al., issued May 5, 1987. Suitable ether polycarboxylates also include cyclic compounds, particularly alicyclic compounds, such as those described in U.S. Pat. No. 3,923,679 Rapko, issued Dec. 2, 1975; U.S. Pat. No. 4,158,635 Crutchfield et al., issued Jun. 19, 1979; U.S. Pat. No. 4,120,874 Crutchfield et al., issued Oct. 17, 1978; and U.S. Pat. No. 4,102,903 Crutchfield et al., issued Jul. 25, 1978.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al., issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing. which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Dispersants

A description of other suitable polyalkyleneimine dispersants which may be optionally combined with the bleach stable dispersants of the present invention can be found in U.S. Pat. No. 4,597,898 Vander Meer, issued Jul. 1, 1986; European Patent Application 111,965 Oh and Gosselink, published Jun. 27, 1984; European Patent Application 111, 984 Gosselink, published Jun. 27, 1984; European Patent Application 112,592 Gosselink, published Jul. 4, 1984; U.S. Pat. No. 4,548,744 Connor, issued Oct. 22, 1985; and U.S. Pat. No. 5,565,145 Watson et al., issued Oct. 15, 1996; all of which are included herein by reference. However, any suitable clay/soil dispersant or anti-redepostion agent can be used in the laundry compositions of the present invention.

In addition, polymeric dispersing agents which include polymeric polycarboxylates and polyethylene glycols, are suitable for use in the present invention. Polymeric polycarboxylate materials can be prepared by polymerizing or copolymerizing suitable unsaturated monomers, preferably in their acid form. Unsaturated monomeric acids that can be polymerize to form suitable polymeric polycarboxylates include acrylic acid, maleic acid (or maleic anhydride), fumaric acid, itaconic acid, aconitic acid, mesaconic acid, citraconic acid and methylenemalonic acids. The presence in the polymeric polycarboxylates herein or monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in U.S. Pat. No. 3,308,067 Diehl, issued Mar. 7, 1967.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000, preferably from about 5,000, more preferably from about 7,000 to 100,000, more preferably to 75,000, most preferably to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal; ammonium and substituted ammonium salts. Soluble acrylate/maleate copolymers of this type are known materials which are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers. Such materials are also disclosed in EP 193,360, including, for example, the 45/45/10 terpolymer of acrylic/maleic/vinyl alcohol.

Another polymeric material which can be included is polyethylene glycol (PEG). PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used, especially in conjunction with zeolite builders. Dispersing agents such as polyaspartate preferably have a molecular weight (avg.) of about 10,000.

Soil Release Agents

The compositions according to the present invention may optionally comprise one r more soil release agents. If utilized, soil release agents will generally comprise from about 0.01%, preferably from about 0.1%, more preferably from about 0.2% to about 10%, preferably to about 5%, more preferably to about 3% by weight, of the composition. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of the laundry cycle and, thus, serve as an anchor for the hydrophilic segments. This can enable stains occuring subsequent to treatment with the soil release agent to be more easily cleaned in later washing procedures.

The following, all included herein by reference, describe soil release polymers suitable for use in the present invention. U.S. Pat. No. 5,843,878 Gosselink et al., issued Dec. 1, 1998; U.S. Pat. No. 5,834,412 Rohrbaugh et al., issued Nov. 10, 1998; U.S. Pat. No. 5,728,671 Rohrbaugh et al., issued Mar. 17, 1998; U.S. Pat. No. 5,691,298 Gosselink et al., issued Nov. 25, 1997; U.S. Pat. No. 5,599,782 Pan et al., issued Feb. 4, 1997; U.S. Pat. No. 5,415,807 Gosselink et al., issued May 16, 1995; U.S. 5,182,043 Morrall et al., issued Jan. 26, 1993; U.S. Pat. No. 4,956,447 Gosselink et al., issued Sep. 11, 1990; U.S. Pat. No. 4,976,879 Maldonado et al. issued Dec. 11, 1990; U.S. Pat. No. 4,968,451 Scheibel et al., issued Nov. 6, 1990; U.S. Pat. No. 4,925,577 Borcher, Sr. et al., issued May 15, 1990; U.S. Pat. No. 4,861,512 Gosselink, issued Aug. 29, 1989; U.S. Pat. No. 4,877,896 Maldonado et al., issued Oct. 31, 1989; U.S. Pat. No. 4,771,730 Gosselink et al., issued Oct. 27, 1987; U.S. Pat. No. 711,730 Gosselink et al., issued Dec. 8, 1987; U.S. Pat. No. 4,721,580 Gosselink issued Jan. 26, 1988; U.S. Pat. No. 4,000,093 Nicol et al., issued Dec. 28, 1976; U.S. Pat. No. 3,959,230 Hayes, issued May 25, 1976; U.S. Pat. No. 3,893,929 Basadur, issued Jul. 8, 1975; and European Patent Application 0 219 048, published Apr. 22, 1987 by Kud et al.

Further suitable soil release agents are described in U.S. Pat. No. 4,201,824 Voilland et al.; U.S. Pat. No. 4,240,918 Lagasse et al.; U.S. Pat. No. 4,525,524 Tung et al.; U.S. Pat. No. 4,579,681 Ruppert et al.; U.S. Pat. No. 4,220,918; U.S. Pat. No. 4,787,989; EP 279,134 A, 1988 to Rhone-Poulenc Chemie; EP 457,205 A to BASF (1991); and DE 2,335,044 to Unilever N. V., 1974; all incorporated herein by reference.

Method of Use

The present invention further relates to a method for removing hydrophobic soils, inter alia, body oils, perspiration and other human body soils form fabric, preferably clothing, said method comprising the step of contacting fabric in need of cleaning with an aqueous solution containing at least 0.01% by weight, of a laundry detergent composition comprising:

A) from about 0.01% by weight of a hydrophobically modified polyamine having the formula:

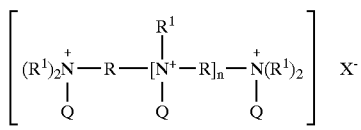

wherein R is $C_5$–$C_{20}$ linear or branched alkylene, and mixtures thereof; $R^1$ is an alkyleneoxy unit having the formula:

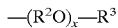

wherein $R^2$ is $C_2$–$C_4$ linear or branched alkylene, and mixtures thereof, $R^3$ is hydrogen, $C_1$–$C_{22}$ alkyl, $C_7$–$C_{22}$ alkylenearyl, an anionic unit, and mixtures thereof; x is from about 15 to about 30; Q is a hydrophobic quaternizing unit selected from the group consisting of $C_8$–$C_3$ linear or branched alkyl, $C_6$–$C_{30}$ cycloalkyl, $C_7$–$C_{30}$ substituted or unsubstituted alkylenearyl, and mixtures thereof; X is an anion present in sufficient amount to provide electronic neutrality, n is from 0 to 4;

B) from about 0.01% by weight, of a surfactant system comprising one or more surfactants selected from:
  i) from 0% to 100% by weight, of one or more anionic surfactants;
  ii) from 0% to 100% by weight, of one or more nonionic surfactants;
  iii) optionally from 0.1% to about 80% by weight, of one or more cationic surfactants,
  iv) optionally from 0.1% to about 80% by weight, of one or more zwitterionic surfactants;
  v) optionally from 0.1% to about 80% by weight, of one or more ampholytic surfactants; or
  vi) mixtures thereof;

C) the balance carriers and adjunct ingredients

Preferably the aqueous solution comprises at least about 0.01% (100 ppm), preferably at least about 1% (1000 ppm) by weight, of said laundry detergent composition.

The compositions of the present invention can be suitably prepared by any process chosen by the formulator, non-limiting examples of which are described in U.S. Pat. No. 5,691,297 Nassano et al., issued Nov. 11, 1997; U.S. Pat. No. 5.574,005 Welch et al., issued Nov. 12, 1996; U.S. Pat. No. 5,569,645 Dinniwell et al., issued Oct. 29, 1996; U.S. Pat. No. 5,565,422 Del Greco et al., issued Oct. 15, 1996; U.S. Pat. No. 5,516,448 Capeci et al., issued May 14, 1996; U.S. Pat. No. 5,489,392 Capeci et al., issued Feb. 6, 1996; U.S. Pat. No. 5,486,303 Capeci et al., issued Jan. 23, 1996 all of which are incorporated herein by reference.

EXAMPLE 1

Synthesis of ethoxylated (E20) bis(hexamethylene) triamine tribenzyl quaternary ammonium bromide Ethoxylation of Bis(hexamethylene)triamine to Average E20 per NH—The ethoxylation is conducted in a 2 gallon stirred stainless steel autoclave equipped for temperature measurement and control, pressure measurement, vacuum and inert gas purging, sampling, and for introduction of ethylene oxide as a liquid. A ~20 lb. net cylinder of ethylene oxide (ARC) is set up to deliver ethylene oxide as a liquid by a pump to the autoclave with the cylinder placed on a scale so that the weight change of the cylinder could be monitored.

A 362 g portion of Bis(hexamethylene)triamine (BHMT) (m.w. 215, (Aldrich), 1.68 moles, 5.04 moles nitrogen, 8.4 moles ethoxylatable (NH) sites, is added to the autoclave. The autoclave is then sealed and purged of air (by applying vacuum to minus 28" Hg followed by pressurization with nitrogen to 250 psia, then venting to atmospheric pressure). The autoclave contents are heated to 80° C. while applying vacuum. After about one hour, the autoclave is charged with nitrogen to about 250 psia while cooling the autoclave to about 105° C. Ethylene oxide is then added to the autoclave incrementally over time while closely monitoring the autoclave pressure, temperature, and ethylene oxide flow rate. The ethylene oxide pump is turned off and cooling is applied to limit any temperature increase resulting from any reaction exotherm. The temperature is maintained between 100 and 110° C. while the total pressure is allowed to gradually increase during the course of the reaction. After a total of 370 grams of ethylene oxide (8.4 moles) has been charged to the autoclave, the temperature is increased to 110° C. and the autoclave is allowed to stir for an additional 2 hours. At this point, vacuum is applied to remove any residual unreacted ethylene oxide.

Next, vacuum is continuously applied while the autoclave is cooled to about 50° C. while introducing 181.5 g of a 25% sodium methoxide in methanol solution (0.84 moles, to achieve a 10% catalyst loading based upon ethoxylatable sites functions). The methoxide solution is removed from the autoclave under vacuum and then the autoclave temperature controller setpoint is increased to 100° C. A device is used to monitor the power consumed by the agitator. The agitator power is monitored along with the temperature and pressure. Agitator power and temperature values gradually increase as methanol is removed from the autoclave and the viscosity of the mixture increases and stabilizes in about 1.5 hours indicating that most of the methanol has been removed. The mixture is further heated and agitated under vacuum for an additional 30 minutes.

Vacuum is removed and the autoclave is cooled to 105° C. while it is being charged with nitrogen to 250 psia and then vented to ambient pressure. The autoclave is charged to 200 psia with nitrogen. Ethylene oxide is again added to the autoclave incrementally as before while closely monitoring the autoclave pressure, temperature, and ethylene oxide flow rate while maintaining the temperature between 100 and 110° C. and limiting any temperature increases due to reaction exotherm. After the addition of 4180 g of ethylene oxide (95 mol, resulting in a total of 20 moles of ethylene oxide per mole of ethoxylatable sites on BHMT), the temperature is increased to 110° C. and the mixture stirred for an additional 2 hours.

The reaction mixture is then collected into a 22 L three neck round bottomed flask purged with nitrogen. The strong alkali catalyst is neutralized by slow addition of 80.7 g methanesulfonic acid (0.84 moles) with heating (100° C.) and mechanical stirring. The reaction mixture is then removed of residual ethylene oxide and deodorized by sparging an inert gas (argon or nitrogen) into the mixture through a gas dispersion frit while agitating and heating the mixture to 120° C. for 1 hour. The final reaction product is cooled slightly and stored in a glass container purged with nitrogen.

Quaternization of BHMT E20 to 90 mol % (3 mol N per mol polymer)—Into a weighed, 1000 ml, 3 neck round bottom flask fitted with argon inlet, condenser, addition funnel, thermometer, mechanical stirring and argon outlet (connected to a bubbler) is added BHMT EO20 (522.8 g, 0.333 mol N, 98% active, m.w.–4615) under argon. The material is heated to 80° C. with stirring until melted. Next, benzyl bromide (61.6 g, 0.36 mol, Aldrich, m.w.–171.04) is slowly added to the melted BHMT EO20 using an addition funnel over a period of 10 minutes. The reaction complete after stirring at 80° C. for 6 hours. The reaction mixture is dissolved in 500 g water and adjusted to pH>7 using 1 N NaOH followed by transfer to a plastic container for storage.

The following are non-limiting examples of the compositions according to the present invention.

TABLE I

| Ingredients | weight % | | | |
|---|---|---|---|---|
| | 2 | 3 | 4 | 5 |
| $C_{14}$–$C_{15}$ alkyl E1.0 sulfate | 22.5 | 22.5 | 22.5 | 22.5 |
| Linear alkyl benzene sulfonate | 3.0 | 3.0 | 3.0 | 3.0 |
| $C_{10}$ amidopropyl DMA | 1.5 | 1.5 | 1.5 | 1.5 |
| $C_{12}$–$C_{14}$ alkyl E7.0 | 3.0 | 3.0 | 3.0 | 3.0 |
| Citric Acid | 2.5 | 2.5 | 2.5 | 2.5 |
| $C_{12}$–$C_{18}$ alkyl fatty acid | 3.5 | 3.5 | 3.5 | 3.5 |
| Rapeseed fatty acid | 5.0 | 5.0 | 5.0 | 5.0 |
| protease | 0.8 | 1.57 | 1.57 | 1.57 |
| amylase | 0.055 | 0.088 | 0.088 | 0.088 |
| cellulase | 0.188 | 0.055 | 0.055 | 0.055 |
| lipolase | 0.06 | — | — | — |
| mannanase | 0.007 | 0.0033 | 0.0033 | 0.0033 |
| Sodium metaborate | 2.0 | 2.5 | 2.5 | 2.5 |
| Ca formate/$CaCl_2$ | 0.02 | 0.10 | 0.10 | 0.10 |
| Modified polyamine[1] | | | | |
| Bleach catalyst[2] | 0.035 | 0.034 | 0.034 | 0.034 |
| Hydrophobic dispersant[3] | 0.65 | 0.76 | 0.76 | 0.76 |
| Soil release agent[4] | 0.147 | — | — | — |
| Soil release agent[5] | — | 0.10 | 0.10 | 0.10 |
| Suds suppresser | 0.60 | 0.60 | 0.60 | 0.60 |
| Water and minors | balance | balance | balance | balance |

[1]Hydrophobically modified polyamine according to Example 1.
[2]1,5-bis(hydroxymethylene)-3,7-dimethyl-2,4-bis(2-pyridyl)-3,7-diazabicyclo[3.3.1]-nonan-9-ol manganese(II) dichloride 1/2$H_2O$.
[3]PEI 189 E15-18 according to U.S. Pat. No. 4,597,898 Vander Meer, issued Jul. 1, 1986.
[4]Soil release agent according to U.S. Pat. No. 4,702,857 Gosselink, issued Oct. 27, 1987.
[5]Soil release agent according to U.S. Pat. No. 4,968,451, Scheibel et al., issued Nov. 6, 1990.

The following examples include compositions which comprise an adjunct bleaching agent.

TABLE II

| Ingredients | weight % | | | |
|---|---|---|---|---|
| | 6 | 7 | 8 | 9 |
| Sodium $C_{11}$–$C_{13}$ alkylbenzene-sulfonate | 13.3 | 13.7 | 10.4 | 11.1 |
| Sodium $C_{14}$–$C_{15}$ alcohol sulfate | 3.9 | 4.0 | 4.5 | 11.2 |
| Sodium $C_{14}$–$C_{15}$ alcohol ethoxylate (0.5) sulfate | 2.0 | 2.0 | — | — |
| Sodium $C_{14}$–$C_{15}$ alcohol ethoxylate (6.5) | 0.5 | 0.5 | 0.5 | 1.0 |
| Tallow fatty acid | — | — | — | 1.1 |
| Sodium tripolyphosphate | — | 41.0 | — | — |
| Zeolite A, hydrate (0.1–10 micron size) | 26.3 | — | 21.3 | 28.0 |
| Sodium carbonate | 23.9 | 12.4 | 25.2 | 16.1 |
| Sodium Polyacrylate (45%) | 3.4 | — | 2.7 | 3.4 |
| Sodium silicate (1:6 ratio $NaO/SiO_2$)(46%) | 2.4 | 6.4 | 2.1 | 2.6 |
| Sodium sulfate | 10.5 | 10.9 | 8.2 | 15.0 |
| Sodium perborate | 1.0 | 1.0 | 5.0 | — |
| Poly(ethyleneglycol), MW ~4000 (50%) | 1.7 | 0.4 | 1.0 | 1.1 |
| Citric acid | — | — | 3.0 | — |
| Bleach catalyst[1] | 0.035 | 0.030 | 0.034 | 0.028 |
| Bleach activator[2] | — | — | 5.9 | — |
| Soil release agent[3] | — | 0.10 | 0.10 | 0.10 |
| Polyamine[4] | | | | |
| Suds suppresser | 0.60 | 0.60 | 0.60 | 0.60 |
| Water and minors[5] | balance | balance | balance | balance |

[1]1,5-bis(hydroxymethylene)-3,7-dimethyl-2,4-bis(2-pyridyl)-3,7-diazabicyclo[3.3.1]-nonan-9-ol manganese(II) dichloride 1/2$H_2O$.
[2]Nonyl ester of sodium p-hydroxybenzene-sulfonate.
[3]Soil release agent according to U.S. Pat. No. 5,415,807 Gosselink et al., issued May 16, 1995.
[4]Hydrophobically modified polyamine according to Example 1.
[5]Balance to 100% can, for example, include minors like optical brightener, perfume, soil dispersant, chelating agents, dye transfer inhibiting agents, additional water, and fillers, including $CaCO_3$, talc, silicates, etc.

The following is a non-limiting example of the bleaching system of the present invention in the absence of a source of hydrogen peroxide.

TABLE III

| Ingredients | weight % | | | |
|---|---|---|---|---|
| | 10 | 11 | 12 | 13 |
| Sodium $C_{11}$–$C_{13}$ alkylbenzene-sulfonate | 13.3 | 13.7 | 10.4 | 11.1 |
| Sodium $C_{14}$–$C_{15}$ alcohol sulfate | 3.9 | 4.0 | 4.5 | 11.2 |
| Sodium $C_{14}$–$C_{15}$ alcohol ethoxylate (0.5) sulfate | 2.0 | 2.0 | — | — |
| Sodium $C_{14}$–$C_{15}$ alcohol ethoxylate (6.5) | 0.5 | 0.5 | 0.5 | 1.0 |
| Tallow fatty acid | — | — | — | 1.1 |
| Sodium tripolyphosphate | — | 41.0 | — | — |
| Zeolite A, hydrate (0.1–10 micron size) | 26.3 | — | 21.3 | 28.0 |
| Sodium carbonate | 23.9 | 12.4 | 25.2 | 16.1 |
| Sodium Polyacrylate (45%) | 3.4 | — | 2.7 | 3.4 |
| Sodium silicate (1:6 ratio $NaO/SiO_2$)(46%) | 2.4 | 6.4 | 2.1 | 2.6 |
| Sodium sulfate | 10.5 | 10.9 | 8.2 | 15.0 |
| Poly(ethyleneglycol), MW ~4000 (50%) | 1.7 | 0.4 | 1.0 | 1.1 |
| Citric acid | — | — | 3.0 | — |
| Bleach catalyst[1] | 0.10 | 0.07 | 0.035 | 0.028 |
| Hydrophobically modified polyamine[2] | | | | |
| Hydrophobic dispersant[5] | 0.65 | 0.76 | 0.76 | 0.76 |
| Soil release agent[6] | 0.147 | 0.10 | 0.10 | 0.10 |
| Suds suppresser | 0.60 | 0.60 | 0.60 | 0.60 |
| Water and minors[7] | balance | balance | balance | balance |

[1]1,5-bis(hydroxymethylene)-3,7-dimethyl-2,4-bis(2-pyridyl)-3,7-diazabicyclo[3.3.1]-nonan-9-ol manganese(II) dichloride 1/2$H_2O$.
[2]Hydrophobically modified polyamine according to Example 1.
[3]Potassium sulfite.
[4]PEI 189 E15-18 according to U.S. Pat. No. 4,597,898 Vander Meer, issued Jul. 1, 1986.
[6]Soil release agent according to U.S. Pat. No. 5,415,807 Gosselink et al., issued May 16, 1995.
[7]Balance to 100% can, for example, include minors like optical brightener, perfume, soil dispersant, chelating agents, dye transfer inhibiting agents, additional water, and fillers, including $CaCO_3$, talc, silicates, etc.

The compositions of the present invention can be suitably prepared by any process chosen by the formulator, non-limiting examples of which are described in U.S. Pat. No. 5,691,297 Nassano et al., issued Nov. 11, 1997; U.S. Pat. No. 5,574,005 Welch et al., issued Nov. 12, 1996; U.S. Pat. No. 5,569,645 Dinniwell et al., issued Oct. 29, 1996; U.S. Pat. No. 5,565,422 Del Greco et al., issued Oct. 15, 1996; U.S. Pat. No. 5,516,448 Capeci et al., issued May 14, 1996; U.S. Pat. No. 5,489,392 Capeci et al., issued Feb. 6, 1996; U.S.

Pat. No. 5,486,303 Capeci et al., issued Jan. 23, 1996 all of which are incorporated herein by reference.

The following are non-limiting examples of nil surfactant compositions according to the present invention.

TABLE IV

|  | weight % | | | |
| --- | --- | --- | --- | --- |
| Ingredients | 14 | 15 | 16 | 17 |
| Ethanol | 3.00 | 2.81 | — | 10.0 |
| Monoethanolamine | 1.50 | 0.75 | 1.00 | 1.00 |
| Propanediol | 8.00 | 7.50 | 10.0 | — |
| Boric Acid | 3.50 | 3.50 | 3.50 | 3.50 |
| Sodium Toluene Sulfonate | 2.50 | 2.25 | 2.50 | 2.50 |
| NaOH | 3.0 | 5.0 | 2.5 | 1.0 |
| citric Acid | 2.5 | 2.5 | 2.5 | — |
| hydrophobically modified polyamine[1] | 3.0 | 3.0 | 1.5 | 5.0 |
| nitrilotriacetic acid | — | — | — | 5 |
| protease | 0.8 | 1.57 | 1.57 | 1.57 |
| amylase | 0.055 | 0.088 | 0.088 | 0.088 |
| cellulase | 0.188 | 0.055 | 0.055 | 0.055 |
| lipolase | 0.06 | — | — | — |
| mannanase | 0.007 | 0.0033 | 0.0033 | 0.0033 |
| Sodium metaborate | 2.0 | 2.5 | — | — |
| Ca formate/CaCl$_2$ | 0.02 | 0.10 | 0.10 | 0.10 |
| Water and minors[2] | balance | balance | balance | balance |

[1]Hydrophobically modified polyamine according to Example 1.
[2]Balance to 100% can, for example, include minors like bleach catalysts inter alia, 1,5-bis(hydroxymethylene)-3,7-dimethyl-2,4-bis(2-pyridyl)-3,7-diazabicyclo[3,3,1]-nonan-9-ol manganese(II) dichloride 1/2H$_2$O, dispersants, inter alia, PEI 189 E15-18 according to U.S. Pat. No. 4,597,898 Vander Meer, issued Jul. 1, 1986, or PEI 1800 E$_7$ according to U.S. Pat. No. 5,565,145 Watson et al., issued Oct. 15, 1996, optical brightener, perfume, suds suppresser, soil release agents, inter alia, according to U.S. Pat. No. 4,702,857 Gosselink, issued Oct. 27, 1987, or U.S. Pat. No. 4,968,451, Scheibel et al., issued Nov. 6, 1990, chelating agents, dye transfer inhibiting agents, additional water, and fillers, including CaCO$_3$, talc, silicates, etc.

The following examples include compositions which comprise an adjunct bleaching agent.

TABLE V

|  | weight % | | | |
| --- | --- | --- | --- | --- |
| Ingredients | 18 | 19 | 20 | 21 |
| Sodium tripolyphosphate | — | 41.0 | — | — |
| Zeolite A, hydrate (0.1–10 micron size) | 26.3 | — | 21.3 | 28.0 |
| Sodium carbonate | 23.9 | 12.4 | 25.2 | 16.1 |
| Sodium Polyacrylate (45%) | 3.4 | — | 2.7 | 3.4 |
| Sodium silicate (1:6 ratio NaO/SiO$_2$)(46%) | 2.4 | 6.4 | 2.1 | 2.6 |
| Sodium sulfate | 10.5 | 10.9 | 8.2 | 15.0 |
| Sodium perborate | 1.0 | 1.0 | 5.0 | — |
| Poly(ethyleneglycol), MW ~4000 (50%) | 1.7 | 0.4 | 1.0 | 1.1 |
| Citric acid | — | — | 3.0 | — |
| Bleach catalyst[1] | 0.035 | 0.030 | 0.034 | 0.028 |
| Bleach activator[2] | — | — | 5.9 | — |
| Soil release agent[3] | — | 0.10 | 0.10 | 0.10 |
| Polyamine[4] | 3.0 | 5.5 | 2.0 | 2.0 |
| Water and minors[5] | balance | balance | balance | balance |

[1]1,5-bis(hydroxymethylene)-3,7-dimethyl-2,4-bis(2-pyridyl)-3,7-diazabicyclo[3.3.1]-nonan-9-ol manganese(II) dichloride 1/2H$_2$O.
[2]Nonyl ester of sodium p-hydrobenzene-sulfonate.
[3]Soil release agent according to U.S. Pat. No. 5,415,807 Gosselink et al., issued May 16, 1995.
[4]Hydrophobically modified polyamine according to Example 1.
[5]Balance to 100% can, for example, include minors like optical brightener, perfume, soil dispersant, chelating agents, dye transfer inhibiting agents, additional water, suds suppressors, and fillers, including CaCO$_3$, talc, silicates, etc.

The following are non-limiting example of a nil surfactant compositions comprising the bleaching system of the present invention in the absence of a source of hydrogen peroxide.

TABLE VI

|  | weight % | | | |
| --- | --- | --- | --- | --- |
| Ingredients | 22 | 23 | 24 | 25 |
| Sodium tripolyphosphate | — | 41.0 | — | — |
| Zeolite A, hydrate (0.1–10 micron size) | 26.3 | — | 21.3 | 28.0 |
| Sodium carbonate | 23.9 | 12.4 | 25.2 | 16.1 |
| Sodium Polyacrylate (45%) | 3.4 | — | 2.7 | 3.4 |
| Sodium silicate (1:6 ratio NaO/SiO$_2$)(46%) | 2.4 | 6.4 | 2.1 | 2.6 |
| Sodium sulfate | 10.5 | 10.9 | 8.2 | 15.0 |
| Poly(ethyleneglycol), MW ~4000 (50%) | 1.7 | 0.4 | 1.0 | 1.1 |
| Citric acid | — | — | 3.0 | — |
| Bleach catalyst[1] | 0.10 | 0.07 | 0.035 | 0.028 |
| Hydrophobically modified polyamine[2] | 3.0 | 3.0 | 3.5 | 2.0 |
| Water and minors[3] | balance | balance | balance | balance |

[1]1,5-bis(hydroxymethylene)-3,7-dimethyl-2,4-bis(2-pyridyl)-3,7-diazabicyclo[3.3.1]-nonan-9-ol manganese(II) dichloride 1/2H$_2$O.
[2]Hydrophobically modified polyamine according to Example 1.
[3]Balance to 100% can, for example, include minors like potassium sulfite, hydrophobic dispersants (inter alia, PEI 189 E15-18 according to U.S. Pat. No. 4,597,898 Vander Meer, issued Jul. 1, 1986), suds suppressors, soil-release agents (inter alia, according to U.S. Pat. No. 5,415,807 Gosselink et al., issued May 16, 1995), optical brightener, perfume, soil dispersant, chelating agents, dye transfer inhibiting agents, additional water, and fillers, including CaCO$_3$, talc, silicates, etc.

The following are non-limiting examples of Automatic Dishwashing Detergent Compositions comprising nil-surfactant.

TABLE VII

|  | weight % | | | |
| --- | --- | --- | --- | --- |
| Ingredients | 26 | 27 | 28 | 29 |
| Sodium tripolyphosphate | 25 | 25 | 50 | 50 |
| Sodium metasilicate pentahydrate | 20 | 25 | 20 | 20 |
| Sodium Sulfate | 15 | 20 | 20 | 15 |
| Hexylene Glycol | 2.0 | — | — | — |
| Sodium carbonate | 20 | 30 | 28 | 20 |
| Hydrophobically modified polyamine[1] | 3.0 | 3.0 | 3.5 | 2.0 |
| Water and minors[2] | balance | balance | balance | balance |

[1]Hydrophobically modified polyamine according to Example 1.
[2]Balance to 100% can, for example, include minors like enzymes, perfume, soil dispersant, chelating agents, metal bleach catalysts, sodium perborate, chlorine bleaching agents, fillers, etc.

What is claimed is:
1. A polyamine having the formula:

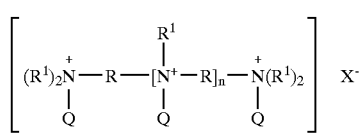

wherein R is $C_6-C_{12}$ linear or branched alkylene, and mixtures thereof; $R^1$ is a alkyleneoxy unit having the formula:

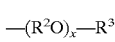

wherein $R^2$ is $C_2-C_4$ linear or branched alkylene, and mixtures thereof; $R^3$ is hydrogen, benzyl, and mixtures thereof; x is from about 15 to about 30; Q is a hydrophobic quaternizing unit selected from the group consisting of $C_8-C_{30}$ linear or branched alkyl, $C_6-C_{30}$ cycloalkyl, and mixtures thereof; X is an anion present in sufficient amount to provide electronic neutrality; n is from 1 to 3.

2. A compound according to claim 1 wherein R is hexylene, $R^2$ is ethylene, $R^3$ is hydrogen, and x is from 18 to 22.

3. A laundry detergent composition comprising:
A) from about 0.01% to about 50% by weight of a hydrophobically modified polyamine having the formula:

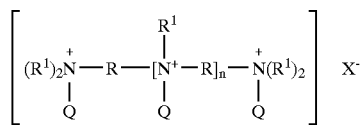

wherein R is $C_6-C_{20}$ linear or branched alkylene, and mixtures thereof; $R^1$ is an alkyleneoxy unit having the formula:

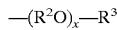

wherein $R^2$ is $C_2-C_4$ linear or branched alkylene, and mixtures thereof; $R^3$ is hydrogen, $C_1-C_{22}$ alkyl, $C_7-C_{22}$ alkylenearyl, and mixtures thereof; x is from 15 to 30; Q is a hydrophobic quaternizing unit selected from the group consisting of $C_8-C_{30}$ linear or branched alkyl, $C_6-C_{30}$ cycloalkyl, $C_7-C_{30}$ substituted or unsubstituted alkylenearyl, and mixtures thereof; X is an anion present in sufficient amount to provide electronic neutrality; n is from 1 to 3;

B) from about 0.01% to about 80% by weight, of a surfactant system comprising one or more surfactants selected from:
 i) from 0% to 100% by weight, of one or more anionic surfactants;
 ii) from 0% to 100% by weight, of one or more nonionic surfactants;
 iii) optionally from 0.1% to about 80% by weight, of one or more cationic surfactants;
 iv) optionally from 0.1% to about 80% by weight, of one or more zwitterionic surfactants;
 V) optionally from 0.1% to about 80% by weight, of one or more ampholytic surfactants; or
 vi) mixtures thereof;

C) the balance carriers and adjunct ingredients.

4. A composition according to claim 3 wherein R is hexylene, $R^2$ is ethylene, 1,2-propylene, and mixtures thereof, $R^3$ is hydrogen, Q is $C_{12}-C_{18}$ linear alkyl, the index x is from 15 to 25, the index n is 1.

5. A composition according to claim 3 wherein said surfactant system comprises from about 0.01% to about 80% by weight, of one or more surfactants selected from:
 i) from 1% to about 100% by weight, of an anionic surfactant selected from:
  a) linear alkyl benzene sulfonates;
  b) mid-chain branched aryl sulfonate surfactants having the formula:

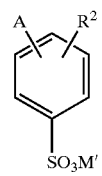

wherein A is a mid-chain branched alkyl unit having the formula:

wherein R and $R^1$ are each independently hydrogen, $C_1-C_3$ alkyl, and mixtures thereof, provided the total number of carbon atoms in said alkyl unit is from 6 to 18 and at least one of R and $R^1$ is not hydrogen, x is an integer from 0 to 13; y is an integer from 0 to 13; z is 0 or 1; $R^2$ is hydrogen, $C_1-C_3$ alkyl, and mixtures thereof; M' is a water soluble cation with sufficient charge to provide neutrality;

c) branched alkyl sulfate surfactants having the formula:

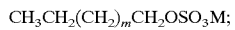

or the formula:

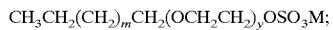

d) mid-chain branched alkyl sulfate surfactants having the formula:

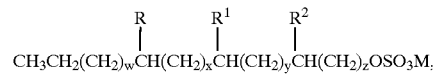

or the formula:

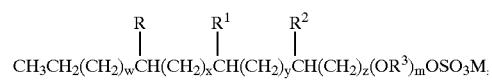

wherein R, $R^1$, and $R^2$ are each independently hydrogen, $C_1-C_3$ alkyl, and mixtures thereof, provided the total number of carbon atoms in said surfactant is from 14 to 20 and at least one of R, $R^1$, and $R^2$ is not hydrogen; the index w is an integer from 0 to 13; x is an integer from 0 to 13; y is an integer from 0 to 13; z is an integer of at least 1; provided w+x+y+z is from 8 to 14 and the total number of carbon atoms in a surfactant is from 14 to 20, $R^3$ is ethylene, 1,2propylene, 1,3-propylene, 1,2-butylene, 1,4-butylene, and mixtures thereof; the average value of the index m is at least 0.01; M is hydrogen, a water soluble cation of sufficient charge to provide electronic neutrality, and mixtures thereof;

ii) from 0% to 100% by weight, of one or nonionic surfactants;
iii) optionally from 0.1% to about 80% by weight, of one or more cationic surfactants;
iv) optionally from 0.1% to about 80% by weight, of one or more zwitterionic iv) optionally from 0.1% to about 80% by weight, of one or more ampholytic surfactants; or vi) mixtures thereof.

6. A composition according to claim 4 wherein said surfactant system comprises from about 0.01% to about 80% by weight, of one or more surfactants selected from:

i) from 1% to about 100% by weight, of an anionic surfactant selected from:
a) linear alkyl benzene sulfonates;
b) mid-chain branched aryl sulfonate surfactants having the formula:

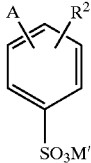

wherein A is a mid-chain branched alkyl unit having the formula:

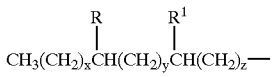

wherein R and $R^1$ are each independently hydrogen, $C_1$–$C_3$ alkyl, and mixtures thereof, provided the total number of carbon atoms in said alkyl unit is from 6 to 18 and at least one of R and $R^1$ is not hydrogen; x is an integer from 0 t 13; y is an integer from 0 to 13; z is 0 or 1; $R^2$ is hydrogen, $C_1$–$C_3$ alkyl, and mixtures thereof; M' is a water soluble cation with sufficient charge to provide neutrality;

c) branched alkyl sulfate surfactants having the formula:

or the formula:

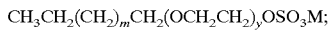

d) mid-chain branched alkyl sulfate surfactants having the formula:

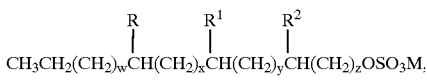

or the formula:

wherein R, $R^1$, and $R^2$ are each independently hydrogen, $C_1$–$C_3$ alkyl, and mixtures thereof, provided the total number of carbon atoms in said surfactant is from 14 to 20 and at least one of $R^1$, $R^1$, and $R^2$ is not hydrogen; the index w is an integer from 0 to 13; x is an integer from 0 to 13; y is an integer from 0 to 13; z is an integer of at least 1; provided w+x+y+z is from 8 to 14 and the total number of carbon atoms in a surfactant is from 14 to 20, $R^3$ is ethylene, 1,2-propylene, 1,3-propylene 1,2-butylene, 1,4-butylene, and mixtures thereof; the average value of the index m is at least 0.01; M is hydrogen, a water soluble cation of sufficient charge to provide electronic neutrality, and mixtures thereof;

ii) from 0% to 100% by weight, of one or more nonionic surfactants;

iii) optionally from 0.1% to about 80% by weight, of one or more cationic surfactants;

iv) optionally from 0.1% to about 80% by weight, of one or more zwitterionic surfactants;

v) optionally from 0.1% to about 80% by weight, of one or more ampholytic surfactants; or vi) mixtures thereof.

7. A composition according to claim 3 further comprising from about 1% to about 80% by weight, of a peroxygen bleaching system comprising:

i) from about 40% to 100% by weight, of the bleaching system, a source of hydrogen-peroxide;
ii) optionally from about 0.1% to about 60% by weight, of the bleaching system, a bleach activator;
iii) optionally from about 1 ppb of the composition, to about 50% by weight of the bleaching system, of a transition-metal bleach catalyst; and
iv) optionally from about 0.1% to about 10% by weight, of a pre-formed peroxygen bleaching agent.

8. A composition according to claim 4 further comprising from about 1% to about 80% by weight, of a peroxygen bleaching system comprising:

i) from about 40% to 100% by weight, of the bleaching system, a source of hydrogen peroxide;
ii) optionally from about 0.1% to about 60% by weight, of the bleaching system, a bleach activator;
iii) optionally from about 1 ppb of the composition, to about 50% by weight of the bleaching system, of a transition-metal bleach catalyst; and
iv) optionally from about 0.1% to about 10% by weight, of a pre-formed peroxygen bleaching agent.

9. A composition according to claim 5 further comprising from about 1% to about 80% by weight, of a peroxygen bleaching system comprising:

i) from about 40% to 100% by weight, of the bleaching system, a source of hydrogen peroxide;
ii) optionally from about 0.1% to about 60% by weight, of the bleaching system, a bleach activator;
iii) optionally from about 1 ppb of the composition, to about 50% by weight of the bleaching system, of a transition-metal bleach catalyst; and
iv) optionally from about 0.1% to about 10% by weight, of a pre-formed peroxygen bleaching agent.

10. A composition according to claim 6 further comprising from about 1% to about 80% by weight, of a peroxygen bleaching system comprising:

i) from about 40% to 100% by weight, of the bleaching system, a source of hydrogen peroxide;
ii) optionally from about 0.1% to about 60% by weight, of the bleaching system, a bleach activator;

iii) optionally from about 1 ppb of the composition, to about 50% by weight of the bleaching system of a transition-metal bleach catalyst; and iv) optionally from about 0.1% to about 10% by weight, of a pre-formed peroxygen bleaching agent.

11. A nil surfactant laundry composition comprising:

a) from about 0.01% to about 50% by weight of a hydrophobically modified polyamine having the formula:

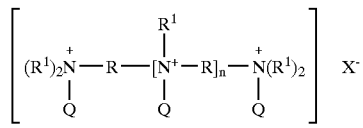

wherein R is $C_6$–$C_{20}$ linear or branched alkylene, and mixtures thereof; $R^1$ is an alkyleneoxy unit having the formula:

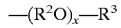

wherein $R^2$ is $C_2$–$C_4$ linear or branched alkylene, and mixtures thereof, $R_3$ is hydrogen, $C_1$–$C_{22}$ alkyl, $C_7$–$C_{22}$ alkylenearyl, and mixtures thereof, x is from 15 to 30; Q is a hydrophobic quaternizing unit selected from the group consisting of $C_8$–$C_{30}$ linear or branched alkyl, $C_6$–$C_{30}$ cycloalkyl, and mixtures thereof; X is an anion present in sufficient amount to provide electronic neutrality; n is from 1 to 3; and b) the balance carriers and adjunct ingredients.

12. A method for cleaning fabric comprising the step of contacting an article of fabric with an aqueous solution containing at least 0.1% by weight of a composition comprising:

A) from about 0.01% to about 50% by weight of a hydrophobically modified polyamine having the formula:

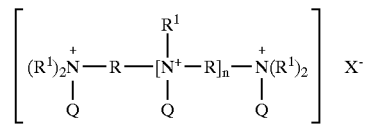

wherein R is $C_6$–$C_{20}$ linear or branched alkylene, and mixtures thereof, $R^1$ is an alkyleneoxy unit having the formula:

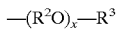

wherein $R_2$ is $C_2$–$C_4$ linear or branched alkylene, and mixtures thereof; $R^3$ is hydrogen, $C_1$–$C_{22}$ alkyl, $C_7$–$C_{22}$ alkylenearyl, and mixture thereof; x is from 15 to 30; Q is a hydrophobic quaternizing unit selected from the group consisting of $C_8$–$C_{30}$ linear or branched alkyl, $C_6$–$C_{30}$ cycloalkyl, and mixtures thereof; X is an anion present in sufficient amount to provide electronic neutrality; n is from 1 to 3;

B) from about 0.01% to about 80% by weight, of a surfactant system comprising one or more surfactants selected from:

i) from 0% to 100% by weight, of one or more anionic surfactants;

ii) from 0% to 100% by weight, of one or more nonionic surfactants;

iii) optionally from 0.1% to about 80% by weight, of one or more cationic surfactants;

iv) optionally from 0.1% to about 80% by weight, of one or more zwitterionic surfactants;

v) optionally from 0.1% to about 80% by weight, of one or more ampholytic surfactants; or vi) mixtures thereof;

C) the balance carriers and adjunct ingredients.

* * * * *